(12) United States Patent
Shyur et al.

(10) Patent No.: US 10,434,132 B2
(45) Date of Patent: Oct. 8, 2019

(54) GALACTOLIPIDS-ENRICHED PLANT EXTRACTS AND THE USES THEREOF

(71) Applicant: ACADEMIA SINICA, Taipei (TW)

(72) Inventors: Lie-Fen Shyur, Taipei (TW); Jia-Hua Feng, Taipei (TW); Maria Karmella Apaya, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/172,428

(22) Filed: Oct. 26, 2018

(65) Prior Publication Data

US 2019/0060388 A1     Feb. 28, 2019

Related U.S. Application Data

(63) Continuation-in-part of application No. 14/295,173, filed on Jun. 3, 2014, now abandoned.

(30) Foreign Application Priority Data

Jun. 4, 2013 (TW) .............................. 102119755 A

(51) Int. Cl.
| | |
|---|---|
| A61K 36/00 | (2006.01) |
| A61K 36/88 | (2006.01) |
| A61K 31/25 | (2006.01) |
| A61K 36/28 | (2006.01) |
| A61K 8/9794 | (2017.01) |
| A61Q 19/02 | (2006.01) |
| A61P 1/16 | (2006.01) |
| A61P 31/04 | (2006.01) |

(52) U.S. Cl.
CPC ............ *A61K 36/88* (2013.01); *A61K 8/9794* (2017.08); *A61K 31/25* (2013.01); *A61K 36/28* (2013.01); *A61K 2236/33* (2013.01); *A61P 1/16* (2018.01); *A61P 31/04* (2018.01); *A61Q 19/02* (2013.01)

(58) Field of Classification Search
CPC ...................................................... A61K 36/00
USPC ............................................................ 424/725
See application file for complete search history.

(56) References Cited

U.S. PATENT DOCUMENTS

2005/0075342 A1*  4/2005  Abe ..................... C07D 487/04
                                                514/248

OTHER PUBLICATIONS

Grace et al., Natural product communication, pp. 126301266, vol. 7, No. 10, 2012.
Murakami et al., J. Agric. Food Chem., 1995, 43, 2779-2783.
Sabha et al., Pharmacology, 2012, 89:260-269.
Takahashi et al., Biosci. Biotechnol. Biochem., 75 (11), 2240-2242, 2011.

* cited by examiner

*Primary Examiner* — Michael V Meller
(74) *Attorney, Agent, or Firm* — Muncy, Geissler, Olds & Lowe, P.C.

(57) ABSTRACT

The present invention is related to a galactolipids-enriched plant extract, prepared by extracting a plant sample selected from a group consisting of: *Gynura divaricata* subsp. *formosana* (Asteraceae) (GD), *Murdannia bracteata* (C. B. Clarke) J. K. Morton ex D. Y. Hong (Commelinaceae) (MB), and *Crassocephalum rabens* S. Moore (Asteraceae) (CR) with a series of solvents. A pharmaceutical, nutritional, or healthcare composition for protecting or treating acute fulminant hepatitis, for protecting or treating sepsis or related indication thereof, and a composition for skin whitening are also provided herein. These compositions all comprise effective amounts of the galactolipids-enriched plant extracts or purified compounds thereof as bioactive ingredients.

1 Claim, 24 Drawing Sheets
(16 of 24 Drawing Sheet(s) Filed in Color)

Fig. 10A

GALACTOLIPIDS-ENRICHED PLANT EXTRACTS AND THE USES THEREOF

CROSS-REFERENCE TO RELATED APPLICATIONS

This application is a Continuation-in-Part of co-pending application Ser. No. 14/295,173 filed on Jun. 3, 2014, for which priority is claimed under 35 U.S.C. § 120; and this application claims priority of Application No. 102119755 filed in Taiwan, R.O.C. on Jun. 4, 2013 under 35 U.S.C. § 119; the entire contents of all of which are hereby incorporated by reference.

FIELD OF THE INVENTION

The present invention relates to a galactolipids-enriched plant extract, especially relates to an extract from *Crassocephalum rabens* (Juss. Ex Jacq.) S. Moore, *Gynura divaricata* subsp. *formosana* and *Murdannia bracteata* (C. B. Clarke) J. K. Morton ex D. Y Hong. This present invention also relates to the uses of the plant extract to produce pharmaceutical composition for protecting or treating acute fulminant hepatitis, sepsis or other related adaptations thereof and skin-whitening agent.

DESCRIPTION OF THE RELATED ART

Recently, researches indicate that many natural ingredients from plants (phytochemicals) have various curative effects. Hereinafter, there are three common plants in Taiwan *Crassocephalum rabens* (Juss. Ex Jacq.) S. Moore, *Gynura divaricata* subsp. *formosana* and *Murdannia bracteata* (C. B. Clarke) J. K. Morton ex D. Y. Hong for illustration.

*Crassocephalum rabens* (Juss. Ex Jacq.) S. Moore (hereinafter "CR") is an ordinary wild vegetable in Taiwan and has great fecundity and adaptivity. The CR belongs to *Crassocephalum* genus of axteraceae family. It tastes like crown daisy and can be collected all over the year. Especially, the taste of the CR is delicious when it collected before blossoming. Medical effects of the CR are known for relieving fever, strengthening stomach, reducing anasarca, and treating stomach ache.

*Gynura divaricata* subsp. *formosana* (hereinafter "GD"), another name of white-red vegetable, is a medical plant belongs to *Gynura* genus of axteraceae family. It is an endemic species at Taiwan growing at coastal region and sometimes at low-elevation mountain of Taiwan. Young stem and leaf of the GD that can be used for food are claimed to have effects for diminishing inflammation, relieving fever, detoxification, diuresis, lowering blood pressure etc.

*Murdannia bracteata* (C. B. Clarke) J. K. Morton ex D. Y. Hong (hereinafter "MB") that is a perennial herb belongs to *Monocotyledons* genus of commelinaceae family mostly grows at side of valley stream, valley water or sand land. It has medical values and is often used for reducing sputum, treating hemorrhoid or treating chronic infection diseases of neck lymph node, acute suppurative infection diseases of hair follicle, sebaceous gland or sweat gland.

However, recent studies are still limited about the active ingredients and the mechanisms of the foresaid three plants. There are no references or patents ever revealed an extract or a purified compound from the foresaid three plants has ability for treating or preventing indications such as hepatitis or septicaemia etc. and skin whitening.

Another way, structure of the galactolipid, also called glycoglycerolipid, which largely exists at nature has two esterified fatty acids at sn-1 and sn-2 position of glycerol and one to four galactoses at sn-3 position. Many natural or synthesis glycoglycerolipids are known for specific bioactivity, including antivirus, antitumor, anti-inflammation and immune depression etc. But this kind of compound is still unclear about its effects to other adaptations and molecular mechanisms of its bioactivity.

SUMMARY OF THE INVENTION

According to prior art, one purpose of the present invention is to provide a method for treating or preventing acute fulminant hepatitis, sepsis and related adaptations thereof or promoting skin whitening, comprising administering a composition of an effective amount of a galactolipids-enriched plant extract or at least one purified object.

Further, the galactolipids-enriched plant extract, which is extracted from a plant sample by using a lower alcohol and then using a lower ester to separate a lower ester extract by partition, then further eluting the lower ester extract by an alcohol elution buffer to have a galactolipids-enriched fraction, wherein the plant sample selected from a group consisting of *Gynura divaricata* subsp. *formosana, murdannia Bracteata* (C. B. Clarke) J. K. Morton ex D. Y Hong, and *Crassocephalum rabens* S. Moore, and the alcohol is 5% to 100% volume percentage of the alcohol elution buffer.

In the embodiments of this present invention, the purified object is 1,2,di-O-α-linolenoyl-3-O-β-galactopyranosyl-sn-glycerol (dLGG) or the purified object consists of three individual compounds of 1,2,di-O-α-linolenoyl-3-O-β-galactopyranosyl-sn-glycerol (dLGG), 1(2)-O-α-linolenoyl-2 (1)-O-α-stearidonoyl 3-O-β-galactopyranosyl-sn-glycerol (dLSG) and 1,2-di-O-α-linolenoyl-3-O-(6-O-α-galactopyranosyl-β-galactopyranosyl)-sn-glycerol (DGDG).

In one embodiment of this present invention, the lower alcohol can be methanol or ethanol.

In an embodiment of this present invention, the lower ester can be ethyl acetate.

In an embodiment of this present invention, the plant extract can further comprise a spectrum of plant extracts. For example, the plant extract is from *Gynura divaricata* subsp. *Formosana*, it can further comprise a chemical fingerprint of *Gynura divaricata* subsp. *formosana*. The plant extract is from *Murdannia bracteata* (C. B. Clarke) J. K. Morton ex D. Y Hong, it can further comprise a chemical fingerprint of *Murdannia bracteata* (C. B. Clarke) J. K. Morton ex D. Y Hong.

In a specific embodiment of this present invention, the ratio of the alcohol in the alcohol elution buffer is about 5%~15%. In another specific embodiment of this present invention, the ratio of the alcohol in the alcohol elution buffer is about 5%~10%. In another specific embodiment of this present invention, the ratio of the alcohol in the alcohol elution buffer is about 10%~15%.

In another embodiment of this present invention, the alcohol elution buffer can comprise dichloromethane and methanol, methanol and water, methanol and acetonitrile, or methanol and acetone.

In a specific embodiment of this present invention, the ratio of dichloromethane and methanol is 9:1 in the methanol elution buffer. The methanol elution buffer with the ratio of 9:1 can be used for elution, for example: to have a lower ether extract from *Gynura divaricata* subsp. *formosana*.

In a specific embodiment of this present invention, the ratio of dichloromethane and methanol is 12:1 in the methanol elution buffer. The methanol elution buffer with the ratio of 12:1 can be used for elution, for example: to have a lower ether extract from *Murdannia bracteata* (C. B. Clarke) J. K. Morton ex D. Y Hong.

In an embodiment of this present invention, the galactolipids-enriched fraction can be further purified by a reversed phase high performance liquid chromatography to have the purified object.

In an embodiment of this present invention, the galactolipids-enriched fraction can comprise, but not limited to, a reversed phase high performance liquid chromatography spectrum (HPLC) of *Crassocephalum rabens* S. Moore shown as FIG. 3.

In an embodiment of this present invention, the galactolipids-enriched fraction can be eluted by an alcohol elution buffer to have the purified object, wherein the alcohol is 70% to 100% volume percentage of the alcohol elution buffer.

In an embodiment of this present invention, the composition further comprises at least one additive, wherein the additive is a pharmaceutically acceptable carrier, excipient, diluent or solvent.

BRIEF DESCRIPTION OF THE DRAWINGS

The patent or application file contains at least one drawing executed in color. Copies of this patent and/or patent application publication with color drawing(s) have been provided to the Office upon request and payment of the necessary fee has been submitted.

FIG. 10A shows the photographs of pellets of B16 melanoma cells after 72 h treatment by 50 μg/mL of kojic acid (KA) or EA fractions derived from total boiling water extracts (CR-W-EA) or total ethanolic extracts (CR-Et-EA) at 25 μg/mL or 50 μg/m L.

DETAILED DESCRIPTION OF THE INVENTION

Figure 1A:
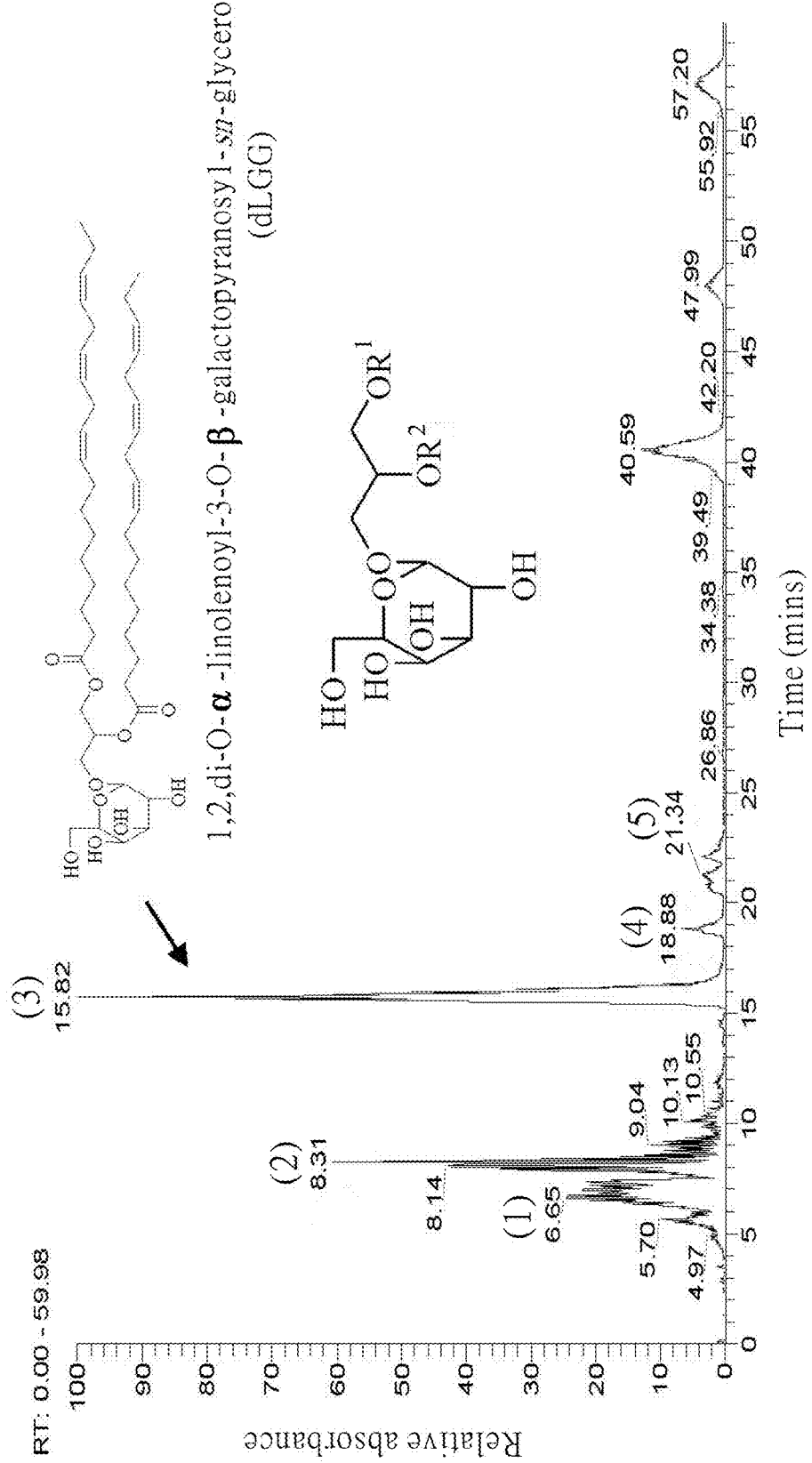
FIG. 1A shows the chemical fingerprinting of the galactolipids-enriched fraction from *Gynura divaricata* subsp. *formosana*. (hereinafter "GDE"). It is total ion chromatogram of the purified object GDE, wherein dLGG was determined as a major component in the fraction.

The term "effective amount, effective amount for preventing and/or treating" means the amount (weight percentage of composition) of the bioactive ingredient (extract or compound) for generating specific effect, preventing and/or treating effect. The person skilled in the art related to this present invention should understand that the effective amount can be different because of reasons such as trying to reach specific effect, to prevent and/or treat the kind of diseases and the way to deliver drugs. Generally, the amount of the bioactive ingredient in compound can be about 1% to about 100% of the weight of the composition, better is about 30% to 100%.

The term "medical, healthy or food acceptable vehicle" includes any standard medical, healthy or food acceptable vehicle. The vehicle that can be solid or liquid depends on the form of pharmaceutical, nutritional addictive or healthy composition. Examples of the solid vehicle include lactose, sucrose, gelatin and agar. Examples of the liquid vehicle include normal saline, buffered saline, water, glycerol and methanol.

The term "purified object" means a purified product from any purification process of a source or a crude product (ex. the plant extract in this present invention).

Embodiment of this present invention is further described with the following examples, but not limited to them. The purposes, features and advantages of this present invention will become more clarify because of the following description and figures.

1. Materials and Methods
1.1 Reagents and Antibodies

D-galactosamine N (D-GaIN), lipopolysaccharide (LPS), silymarin, simvastatin, kojic acid (KA) and dimethyl sulfoxide (DMSO) were purchased from Sigma Chemical Co. (St. Louis, Mo.). Prestained protein markers (Bioman, Taipei, Taiwan) were used to estimate the molecular weight markers of SDS-PAGE. The example of this present invention also used the primary antibodies against tyrosinase, microphthalmia-associated transcription factor (MITF) (Santa Cruz Biotechnology) and F4/80 antibody (eBioscience). Recombinant mice TNT-α, and ELISA kit for measuring TNT-α and IL-6 were from R&D Systems, Inc. (Minneapolis, Minn.). Commercial kits purchased from Randox Laboratories (UK) were used to test the activity of serum aspartate aminotransferase (AST) and alanine aminotransferase (ALT). All other chemicals and solvents were of reagent or high-pressure liquid chromatography (HPLC) grade.

1.2 Cell Culture

B16 melanoma cell line was obtained from ATCC (Manassas, Va.) and grown in RPMI medium 1640 (Gibco/BRL) supplemented with 10% heat-inactivated fetal bovine serum, 100 unit/mL penicillin and 100 μg/mL streptomycin, at 37° C. in a humidified 5% $CO_2$ incubator.

1.3 Depigmentation Assay

B16 melanoma cell line was plated on to 10 cm culture dishes at an initial density of $1 \times 10^5$ cells $dish^{-1}$ and then cultured under the same condition described above. After 12 hours of seeding, the cells were treated by vehicle DMSO, kojic acid (KA), ethyl acetate (EA) fractions of CR's water and ethanolic extractions (Hou et al., 2007) for 72 hours. These cells were harvested by centrifuge and visually evaluated the color of these cell pellets. In another experiment, depigmentation effect of the single compound dLGG was observed and evaluated at different time points with the same procedure.

1.4 Animals

Female C57BL/6J mouse or female ICR mouse (4-week-old) were supplied from National Laboratory Animal center (Taipei, Taiwan) and given a standard laboratory diet and distilled water ad libitum and kept on a 12-hours light/dark cycle at 22±2° C. The embodiment in this present invention was proceed following the institutional guideline and approved by the Institutional Animal Care and Utilization Committee of Academia Sinica, Taiwan.

1.5 Plant Extracts and dLGG Preparation

Preparation of extracts from CR, MB, and GD were followed the protocol previously published by Hou et al. (Hou et. al, Cancer Research 67, 6907-6915, 2007) with some modifications. About 15 kg of fresh whole plant was extracted by 2-3 times weight of 95% ethanol at room temperature. Ethyl acetate was used to partition total ethanolic extracts to produce the ethyl acetate (EA) fraction (GD: 8.6 kg; MB: 8.9 kg). Furthermore, dichloromethane-methanol was used to eluting a silica gel column for separating the EA fraction of GD and MB for yielding 10 subfractions respectively, wherein the elution ratio of methanol to dichloromethane for GD was 1:9, for MB was 1:12 and for CR was 1:9. For GD, subfraction 7 (817 g) was further purified using a Diaion HP-20 gel column eluted with 95% ethanol to give a monogalactosyldiacyl glycerols-enriched fraction (designated GDE; 253.3 g). For MB, subfraction 6 (1.06 kg) was further purified using a Diaion HP-20 gel column eluted with 95% ethanol to give a monogalactosyldiacyl glycerols-enriched fraction (designated MBE; 360.1 g).

RP-HPLC/APCI-M was used to determine the chemical fingerprinting of the enriched fractions. Compound characterization was done using $^1H$ and $^{13}C$ nuclear magnetic resonance (NMR) together with APCI/MS, using a Bruker ADVANCE 500 AV NMR spectrometer and Thermo Finnigan/LCQ Advantage mass spectrometer running in positive ion mode, respectively.

And then, reversed phase HPLC was conducted under the following column and condition to have CR-EA fraction and chemical spectrum thereof. The column was semi-preparative column (Phenomenex 5 μm, C18, 250×4.6 mm) and the condition was to carry on isocratic elution by 98% methanol, 1 mL/min velocity of flow. The dLGG, 1(2)-O-α-linolenoyl-2(1)-O-α-stearidonoyl 3-O-β-galactopyranosyl-sn-glycerol (dLSG) and 1,2-di-O-α-linolenoyl-3-O-(6-O-α-galactopyranosyl-β-galactopyranosyl)-sn-glycerol (DGDG) shown at HPLC spectrums were taken as the indicated compounds of bioactive EA fractions.

GDE's or MBE's HPLC spectrum could be done through the same protocol to treat galactolipids-enriched fractions of GDE or MBE (eluting it by methanol-dichloromethane, wherein the ratio of ethanol to dichloromethane was about 9:1 to 8:2).

1.6 Protection Effects of dLGG or dLGG Containing Plant Extracts on Acute Fulminant Hepatitis in Mice-Induced by LPS/D-GaIN The hepatoprotective effect in live body of compound dLGG isolated from *Crassocephalum rabens* (Asteraceae) in LPS/D-GaIN-induced fulminant hepatitis were investigated and compared with the hepatoprotective drug, silymarin (SM). Mice were randomly separated into four groups (n=6 per group) for treatments: vehicle; LPS/D-GaIN; 50 mg/kg of silymarin (Post-SM50); and 10 mg/kg dLGG (post-dLGG10), and all treatments were given intraperitoneally. One hour after the mice treated with 500 ng LPS and 250 μL saline containing 25 mg D-GaIN (Huang et al., 2012), the dLGG and silymarin were given intraperitoneally. Besides, the other two groups of mice were treated dLGG or silymarin continuously for three days to perform the protection effect of dLGG against LPS/D-GaIN induced fulminate hepatitis. Eight hours after LPS/D-GaIN injection, blood samples were collected through retro-orbital bleeding, and then all mice were sacrificed to collect blood samples and liver tissues.

1.7 Protection or Treatment Effect of dLGG or dLGG Containing Plant Extract on Sepsis in t Mice-Induced by LPS The therapeutic effect of dLGG or dLGG containing CR extracts was estimated by inducing acute inflammation and septic shock using LPS, and the simvastatin (Simva) was used as positive control group. Mice were randomly separated into different treatment groups: vehicle, 10 mg/kg LPS, 10 mg/kg simvastatin (Simva 10), 10 mg/kg CR-EA extraction (CR-EA 10), 50 mg/kg CR-EA extract (CR-EA 50), 5 mg/kg dLGG (dLGG 5) and 25 mg/kg dLGG (dLGG 25). The plant components or the drugs were all injected an hour before administration of LPS. Another animal group was only treated with 25 mg/kg dLGG (dLGG 25 only). All groups were sacrificed after 24 hours and blood samples were collected by retro-orbital bleeding before scarification of mice and organ tissues were collected immediately.

1.8 Histology and Immunohistochemistry Method

Liver, lung and kidney tissues were fixed in 10% buffered formalin then it were embedded into paraffin. The paraffin-embedded tissues were sliced (8-μm) and stained by hematoxylin and eosin (H&E). Besides, sections of paraffin-embedded liver and lung (4-μm for thickness) were heat immobilized and deparaffinized by use of xylene and rehydrated in a graded series of ethanol with a final wash in distilled water, and finally soaked into decloaking chamber (Biocare Medical) containing Target Retrieval Solution (DakoCytomation) for antigen retrieval.

In situ detection of apoptotic cells was conducted according to the manufacturer's protocol (Chemicon). It is using terminal deoxynucleotidyl transferase to work on nucleotide sequence to form a nick at dUTP position for terminal deoxynucleotidyl transferase-mediated dUTP nick end labeling. Finally, AxioVision software (Carl Zeiss MicroImaging, Inc.) was used to analyze the number of TUNEL-positive cells.

Immunohistochemistry with liver, lung and kidney tissues were done by incubating the samples into F4/80 primary antibody for overnight respectively. After subsequent washing, each of the samples was incubated using florescent-labeled secondary antibody. Florescent images of the macrophage cell infiltration (positive F4/80 stained cell) were captured by AxioVision software (Carl Zeiss MicroImaging, Inc.) and then analyzed.

1.9 Western Blot

The liver tissue (0.1 g) of each mouse was estimated by homogenization in a mixer ball mill (MM301, Retsch, Haan, Germany) for 2 minutes, extracted by adding 0.4 mL lysis buffer and centrifuged at 15,000× g for 30 min at 4° C. (Shyur et al., 2008). The supernatant was collected, and total protein concentration of the sample was determined by DC protein test kit (Bio-rad). Protein was resolved by 5%~20% gradient SDS-PAGE and then transferred to membrane and immunoblotted with enhanced chemiluminescence reagents (ECL, Amersham) and monoclonal antibodies against specific protein.

The cellular proteins were produced according to previously published method (Chiang et al., 2005). Protein content was measured by Bradford method (Bio-Rad).

1.10 Measurement of Serum AST and ALT Activity

Blood samples of tested mice were centrifuged under 4° C., 1400× g for 15 minutes to separate serum from blood. Commercial kit purchased from Randox Laboratories (UK) was used to determine the activity of aspartate aminotransferase (AST) and alanine aminotransferase (ALT) in serum supernatants.

1.11 Measurement of Serum IL-6 and TNF-α

Serum levels of interleukin (IL-6) and tumor necrosis factor-alpha (TNF-α) were determined using a commercial kit from eBioscience.

1.12 Statistical Analysis

All data are expressed as means±standard error of the mean (SEM). Differences were compared by ANOVA. Different letter superscripts indicate significant difference within treatments; $P<0.05$ was considered statistically significant.

2. Results 2.1 Chemical Fingerprints for Three Food or Pharmaceutical Plant of *Gynura divaricata* subsp. *formosana* (Asteraceae) and *Murdannia bracteata* (C. B. Clarke) (Commelinaceae)

RP-HPLC and atmospheric chemical ionization-mass spectrometry (ACPI-MS) were used to establish the chemical fingerprints of purified object GDE and MBE. All monogalactosyldiacylglycerol constituents present in the galactolipids-enriched fractions of GDE and MBE were identified. As shown in FIG. 1 and table 1, 1,2,di-O-α-linolenoyl-3-O-β-galacto pyranosyl-sn-glycerol (dLGG) was identified the major component of CD. As shown in FIG. 2 and table 2, dLGG was identified the major component of MB.

Figure 3A:
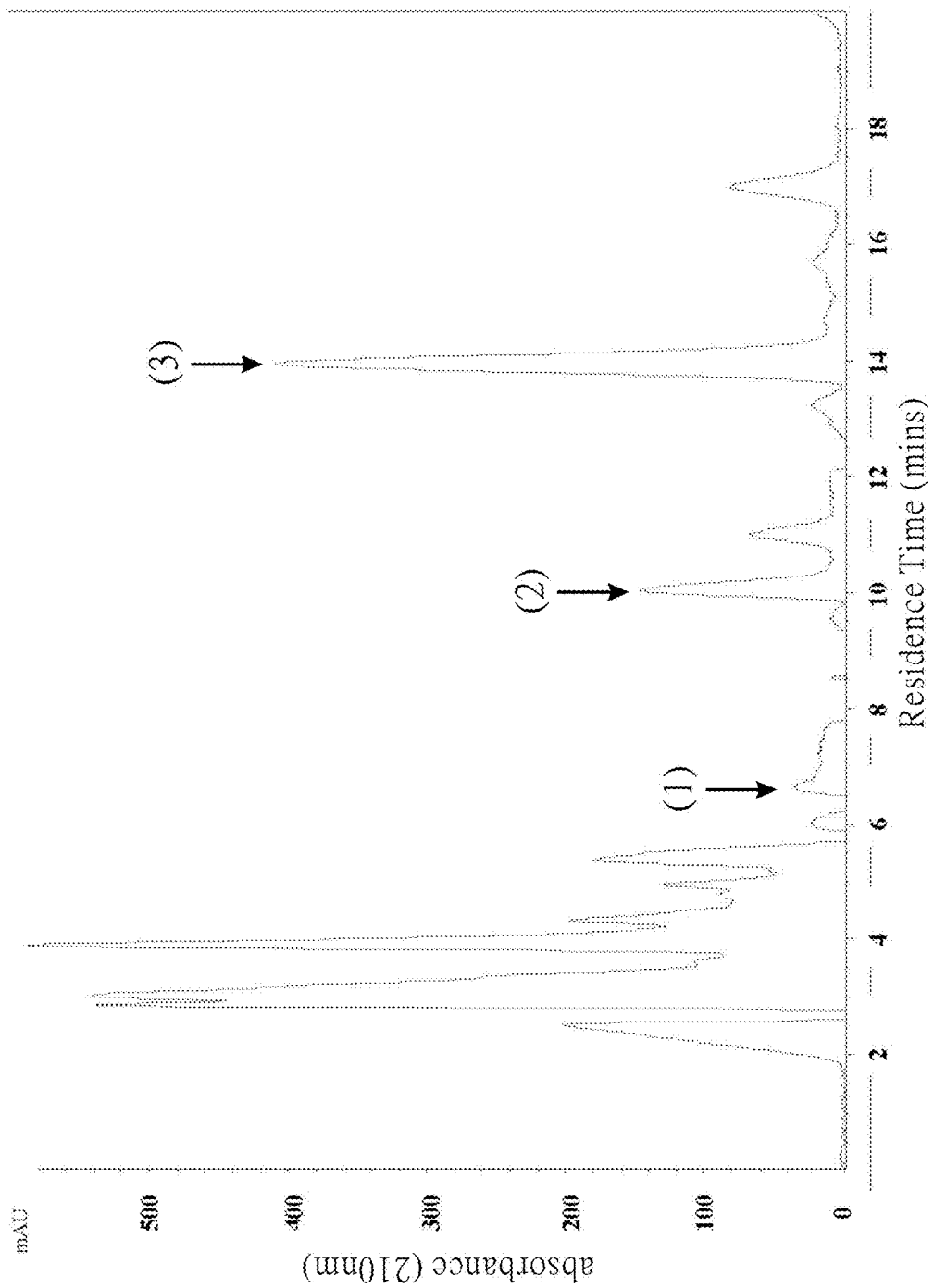
FIG. 3A shows the HPLC spectrum of the ethyl acetate solution from *Crassocephalum rabens* (Juss. Ex Jacq.) S. Moore (hereinafter "CR-EA").
Figure 3B:
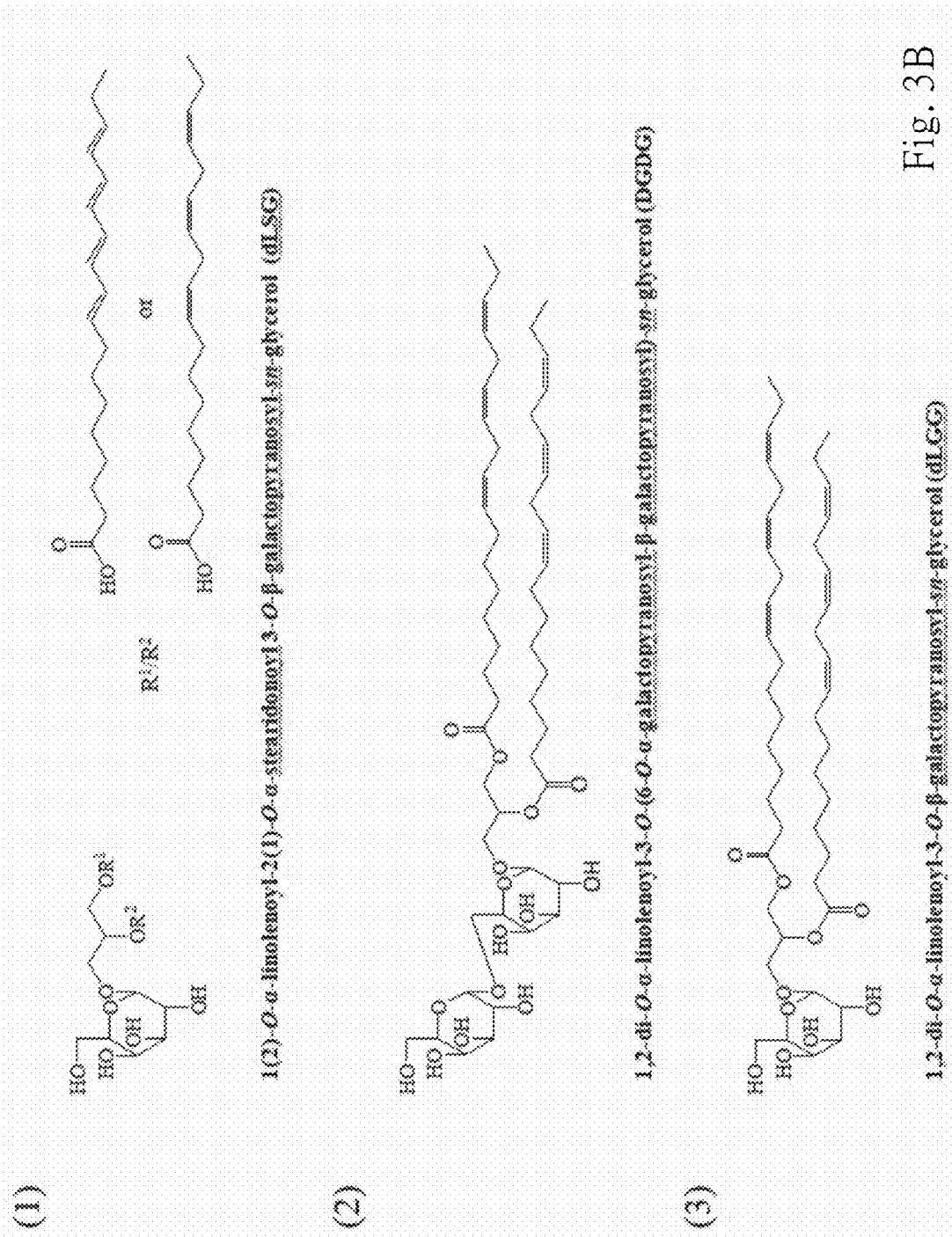
FIG. 3B shows the chemical structures of constituents (1-3) of CR-EA.

The chemical fingerprint of CR-EA, shown in FIG. 3, was taken by RP-HPLC, wherein dLGG, 1(2)-O-α-linolenoyl-2(1)-O-α-stearidonoyl 3-O-β-galactopyranosyl-sn-glycerol (dLSG) and 1,2-di-O-α-linolenoyl-3-O-(6-O-α-galactopyranosyl-β-galactopyranosyl)-sn-glycerol (DGDG) were the indication compounds in the bioactive EA fraction (CR-EA) of CR.

Figure 2A:
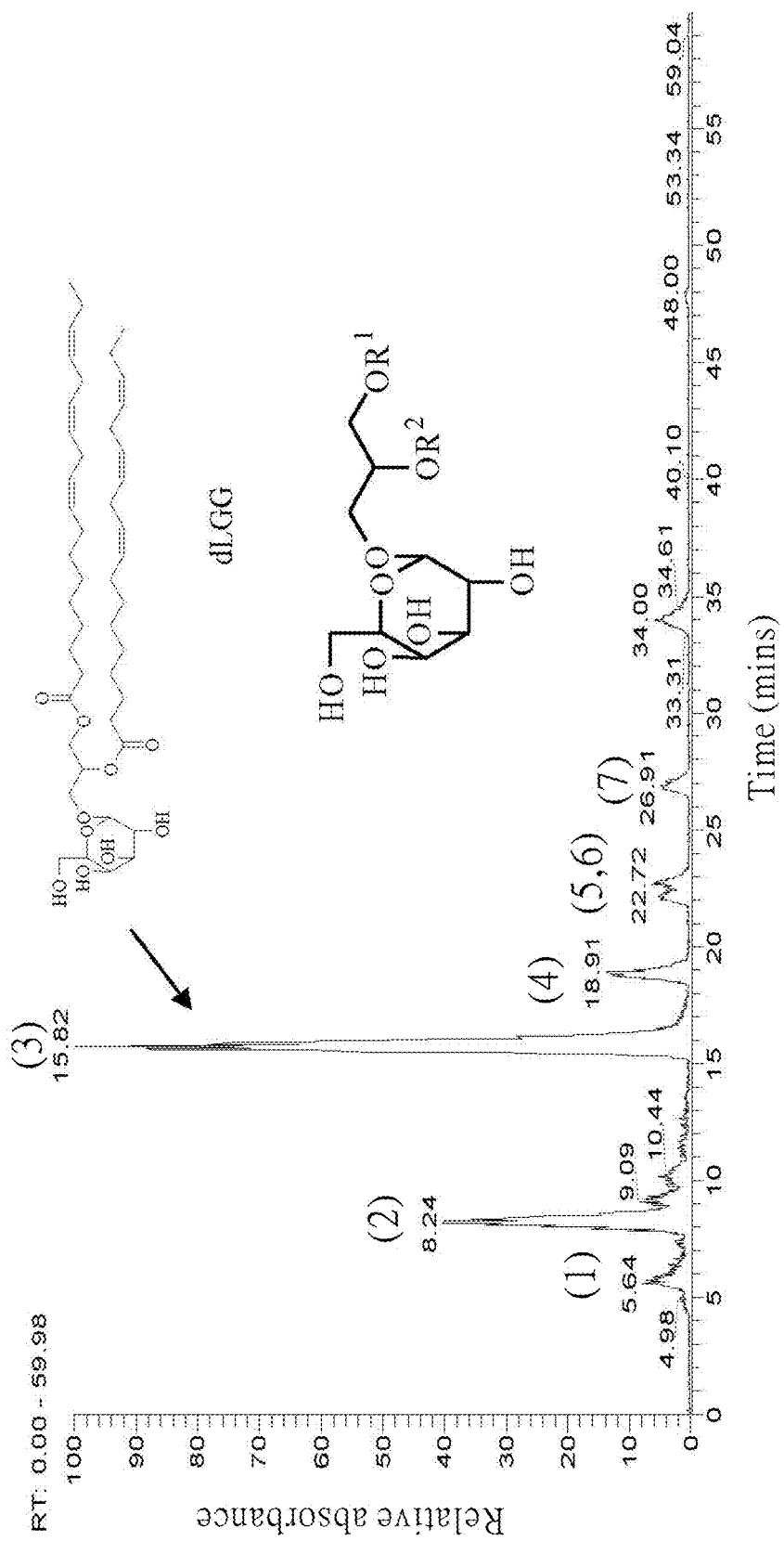
FIG. 2A shows the chemical fingerprinting of the galactolipids-enriched fraction from *Murdannia bracteata* (C. B. Clarke) J. K. Morton ex D. Y. Hong (hereinafter "MBE"). It is total ion chromatogram of the purified object MBE, wherein dLGG was determined as a major component in the fraction.

FIG. 1A and FIG. 2A show the compound peak distribution on the total ion chromatogram of GDE and MBE respectively. Five galactolipid compounds were found in GDE with the fatty acid moieties identified as 18:3/18:3 (dLGG), 18:4/18:4 (1), 18:3/18:4 (2), 18:2/18:3 (4), 16:0/18:3 (5). Meanwhile, the fatty acid moieties of the seven galactolipid compounds in MBE were identified as 18:3/18:3 (dLGG), 18:4/18:4 (1), 18:3/18:4 (2), 18:2/18:3 (4), 16:0/18:3 (5), 18:1/18:3 (6), and 16:0/18:2 (7). It is not confirmed that the sn positioning of the two fatty acid moieties in the compounds 2, 4, 5, 6 and 7.

The m/z of the Na$^+$ adduct [M+Na]$^+$ and fragment ions corresponding to the diacylglycerol, monoacylglycerol, and fatty acid moieties from ACPI-MS are tabulated in tables 1 and 2. Herein, the meanings of abbreviations in tables 1 and 2 are as the following: 18:3, α-Linolenic Acid; 18:2, α-Linoleic acid; 18:1, Oleic acid; 16:0, palmitic acid. The peak percentage was calculated by the following formula:

%=each peak area/peak area of total monogalactosyldiacylglycerol compounds×100%

TABLE 1

APCI-MS data of five major monogalactosyl diglyceride compounds in GDE fraction

| Ion peak | dLGG(3) | peak 1 | 2 | 4 | 5 |
|---|---|---|---|---|---|
| m/z [M + Na]$^+$ Diacylglycerol moieties | 797(4) | 793(1) | 795(6) | 799(3) | 775(1) |
| $[CH_2(OR^1)CH(OR^2)CH_2OH_2]^+$ | 613(100) | 609(100) | 611(100) | 615(100) | 591(100) |
| $[CH_2(OR^1)CH(OR^2)CH_2]^+$ Monoacylglycerol moieties | 595(13) | 591(43) | 593(13) | 597(13) | 573(15) |
| $[CH_2(OR^1)CH(OH)CH_2]^+$ | 335(3) | 333(3) | 335(3) | 337(4) | 313(11) |
| $[CH_2(OH)CH(OR^2)CH_2]^+$ Acyl moieties | | | 333(4) | 335(5) | 353(3) |
| $[R^1]^+$ and $[R^2]^+$ | 261(23) | 259(30) | 261(32) | 263(24) | 239(22) |
| | | | 259(26) | 261(26) | 261(17) |
| Residence time (min) | 15.82 | 6.65 | 8.31 | 18.88 | 21.34 |
| Molecular species (fatty acid/fatty acid) | 18:3/18:3 | 18:4/18:4 | 18:3/18:4 | 18:2/18:3 | 16:0/18:3 |
| % (peak percentage) | 88.1 | 3.2 | 7.5 | 1.0 | 0.1 |

TABLE 2

APCI-MS data of five major monogalactosyl diglyceride compounds in MBE fraction.

| | dLGG(3) | Ion peak Peak 1 | 2 | 4 | 5 | 6 | 7 |
|---|---|---|---|---|---|---|---|
| m/z [M + Na]$^+$ Diacylglycerol moieties | 797 (1) | 793 (1) | 795 (5) | 799 (3) | 775 (4) | 801 (5) | 777 (10) |
| $[CH_2(OR^1)CH—(OR^2)CH_2OH_2]^+$ | 613 (100) | 609 (100) | 611 (100) | 615 (100) | 591 (23) | 617 (100) | 593 (100) |
| $[CH_2(OR^1)CH—(OR^2)CH_2]^+$ Monoacylglycerol moieties | 595 (11) | 591 (14) | 593 (6) | 597 (9) | 573 (7) | 599 (30) | 575 (6) |
| $[CH_2(OR^1)CH—(OH)CH_2]^+$ | 335 (5) | 333 (3) | 335 (5) | 337 (3) | 313 (9) | 339 (10) | 313 (24) |
| $[CH_2(OH)CH—(OR^2)CH_2]^+$ Acyl moieties | | | 333 (7) | 335 (3) | 335 (4) | 335 (8) | 337 (10) |
| $[R^1]^+$ and $[R^2]^+$ | 261 (22) | 259 (24) | 261 (29) | 263 (21) | 239 (22) | 265 (10) | 239 (21) |
| | | | 259 (21) | 261 (17) | 261 (15) | 261 (16) | 263 (30) |
| Residence time (min) | 15.82 | 5.64 | 8.24 | 18.91 | 22.72 | 22.72 | 26.91 |
| Molecular species (fatty acid/fatty acid) | 18:3/18:3 | 18:4/18:4 | 18:3/18:4 | 18:2/18:3 | 16:0/18:3 | 18:1/18:3 | 16:0/18:2 |
| % (peak percentage) | 78.9 | 1.9 | 12.2 | 2.2 | 1.2 | 1.2 | 2.4 |

Figure 1B:
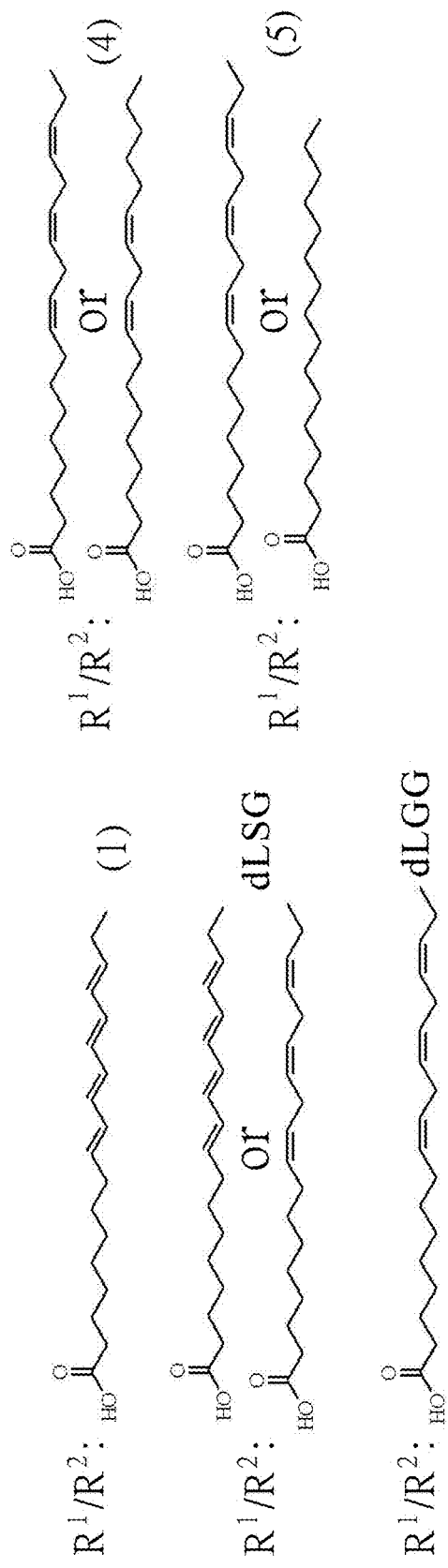
FIG. 1B is the chemical structures of monogalactosyldiacylglycerol constituents (1-5) of GDE.
Figure 2B:
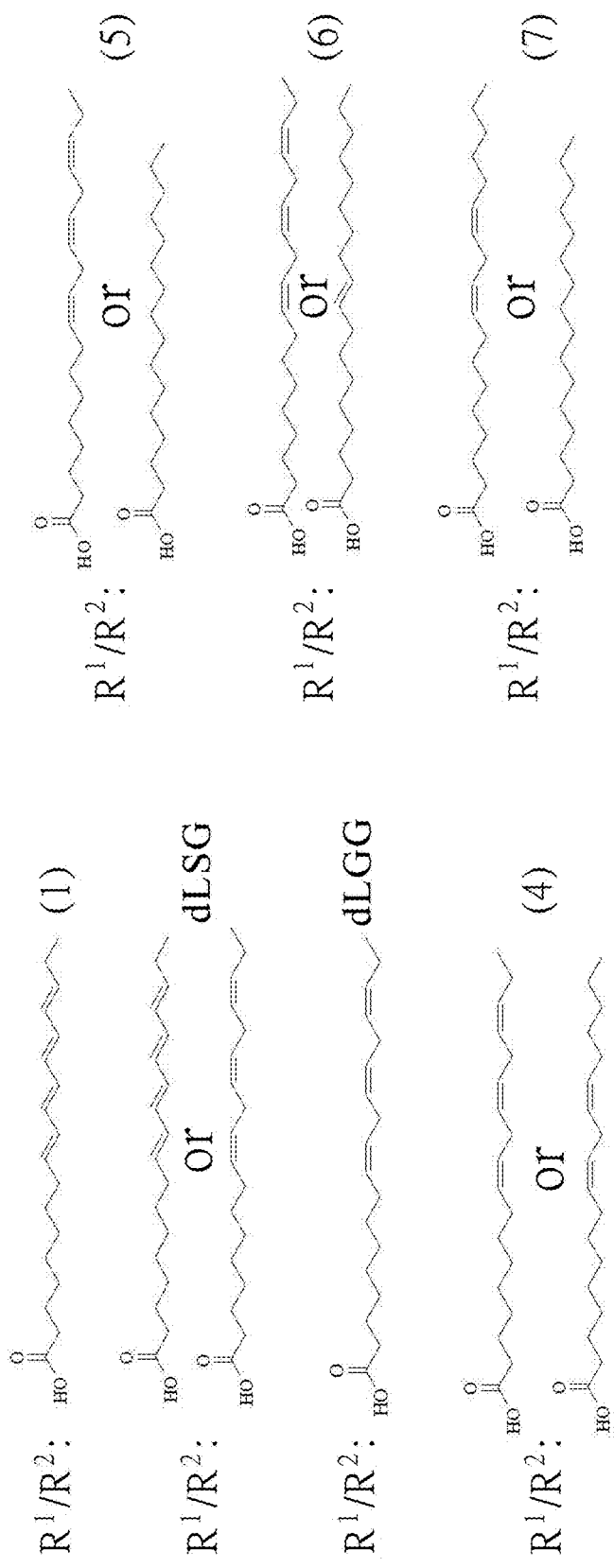
FIG. 2B is the chemical structures of monogalactosyldiacylglycerol constituents (1-7) of MBE.

FIG. 1B and FIG. 2B show the chemical structures of monogalactosyldiacylglycerols in GDE and MBE fractions respectively. The major and active constituent compound is dLGG with the enriched fractions containing 88.1% (*G. divaricata* Subsp. *Formosana*), and 78.9% (*M. bracteata*). And dLGG was determined as 65.7% in the purified object of *C. rabens* (Hou et al., 2007). Furthermore, FIG. 1 to FIG. 3 also shown dLSG and DGDG were in the purified object. With dLGG, dLSG and DGDG as the three indication compounds of galactolipids-enriched fraction extracted from the three pharmaceutical plants in this present invention, the developed chemical fingerprint profiling method can be used to ensure the consistency of the batch-to-batch preparations of the purified objects and can be the protocol for regular quality assurance.

2.2 dLGG as a Therapeutic Agent for Acute Fulminant Hepatitis of LPS/D-GaIN Induced Mice Fulminant hepatic failure (FHF), synonymous with acute liver failure, is related to severe liver disorders that results in rapid distortion of hepatic function that often leads to devastating consequences (Sass and Shakil, 2005). It is a life-threatening disease, with orthotopic liver transplantation as the only curative treatment at present (Russo & Parola, 2011).

LPS/D-GaIN induced mice to cause acute fulminant hepatitis can be a widely used animal model to mimic the cascaded events of FHF observed in clinic (Kosai et al, 1999). This present invention uses this model to evaluate the therapeutic effect of dLGG, a bioactive compound isolated from MB, CR and GD, and the dLGG-enriched galactolipid fractions GDE and MBE on liver injury.

At the same time, a commercial hepatoprotective drug, silymarin (SM), was used as a reference control. Mice were given LPS/D-GaIN 1 hour before intraperitoneal injection of vehicle control 0.5% DMSO, dLGG (10 mg/kg) and SM (50 mg/kg). Mice blood sera from different groups were collected to measure the two clinical indicators of hepatic injury or dysfunction, aspartate aminotransferase (AST) and alanine am inotransferase (ALT) activities.

Figure 4A:
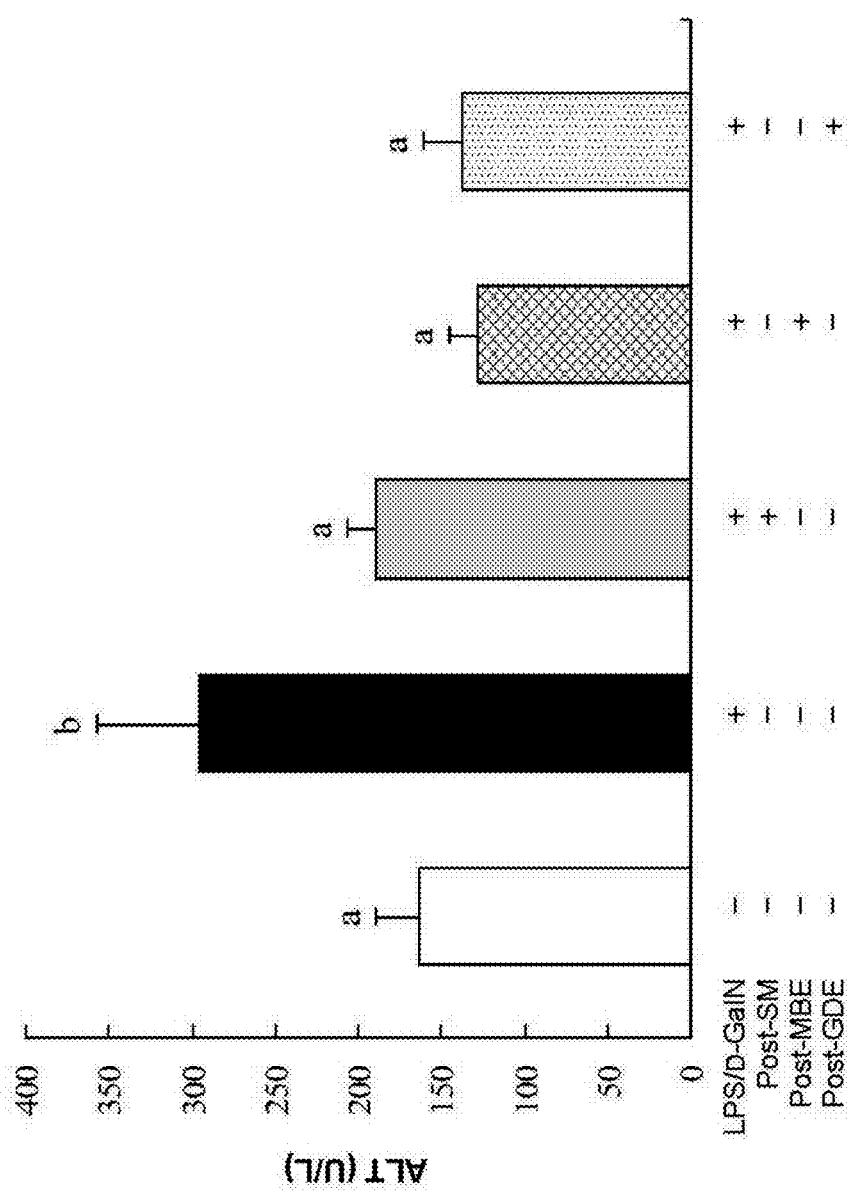
FIG. 4A shows the serum levels of alanine aminotransferase (ALT) in the groups from left to right of vehicle (−),LPS/D-GaIN-challenged mice (LPS/D-GaIN+), LPS/D-GaIN-challenged mice with SM (LPS/D-GaIN+, Post-SM+), LPS/D-GaIN-challenged mice with plant extract MBE (LPS/D-GaIN+, Post-MBE+), LPS/D-GaIN-challenged mice with plant extract GDE (LPS/D-GaIN+, Post-GDE+). Data are mean±S.E.M. of results of 6 mice per treatment group. Different letters indicate the significant difference within the tested groups (P<0.05).
Figure 4B:
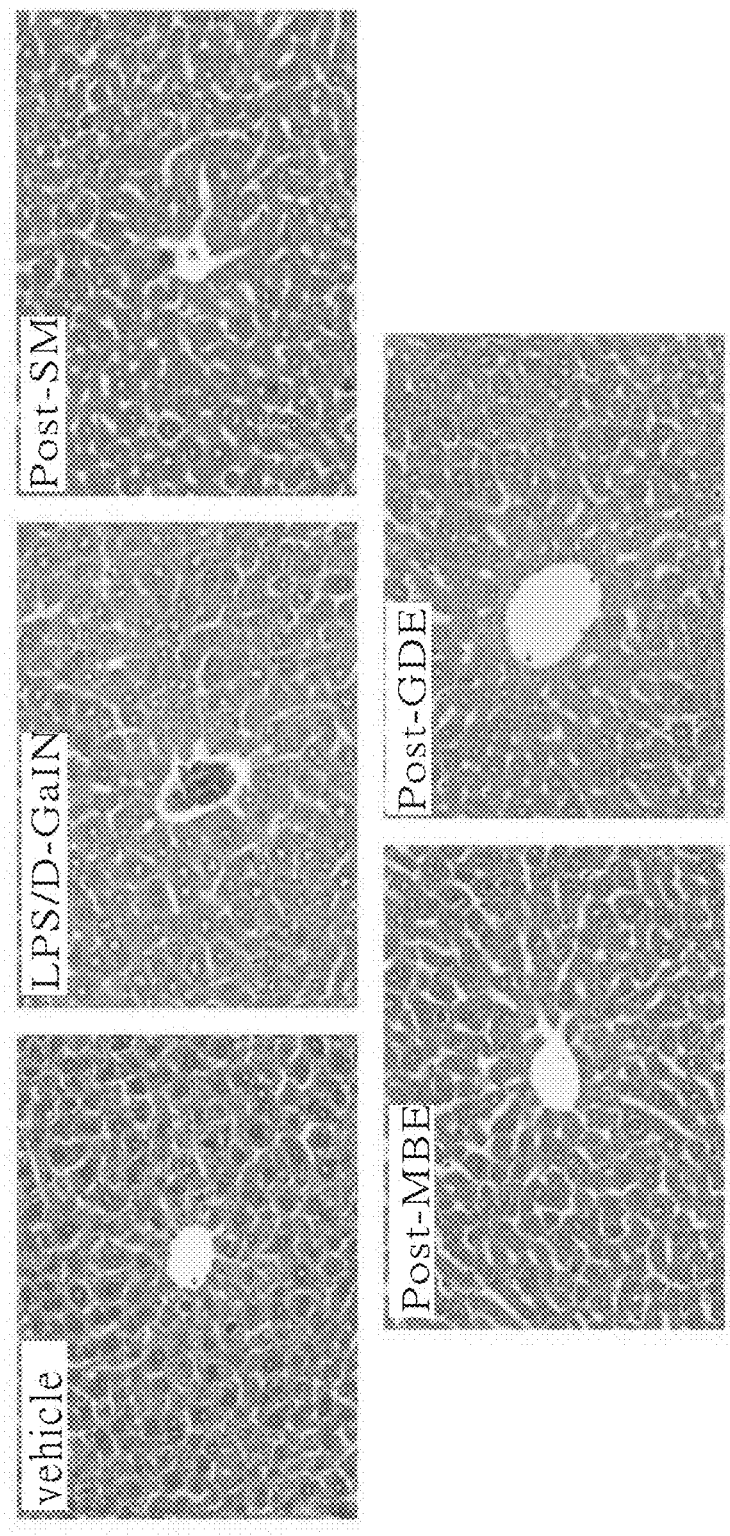
FIG. 4B shows the H&E staining and histology of liver sections from treated mice.
Figure 5A:
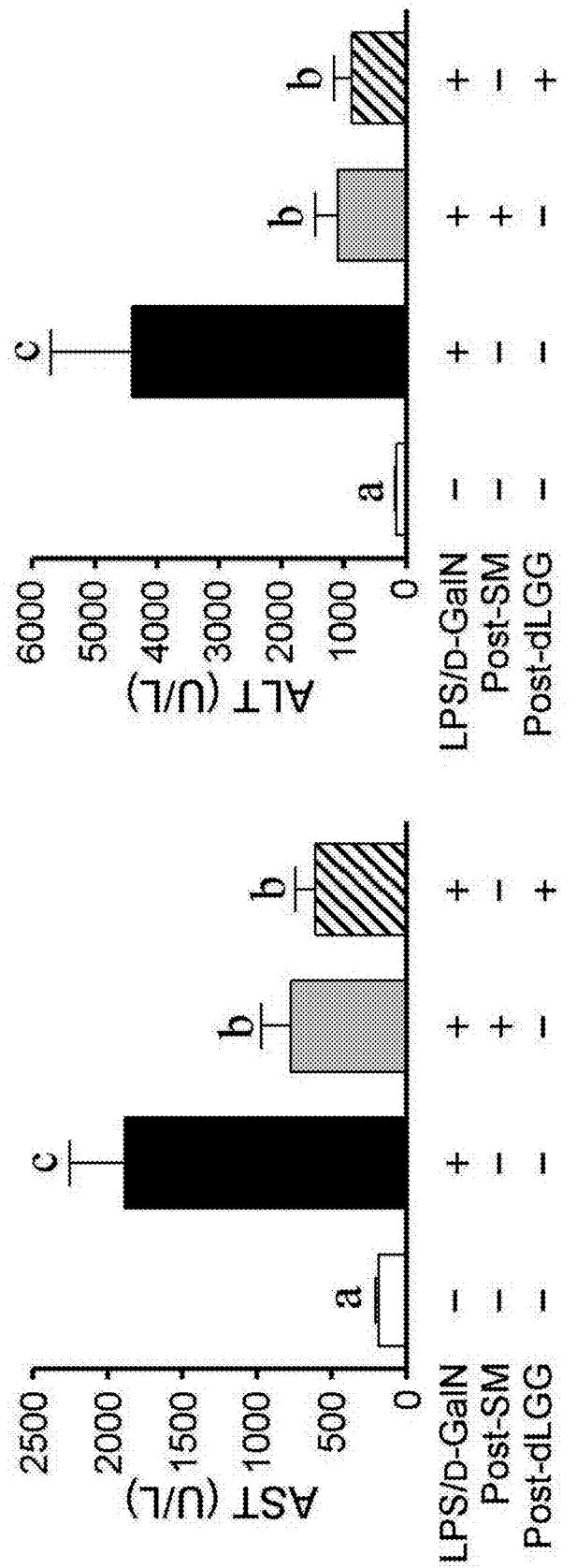
FIG. 5A shows the serum levels of aspartate aminotransferase (AST) and ALT in the groups from left to right of vehicle (−), LPS/D-GaIN-challenged mice (LPS/D-GaIN+), LPS/D-GaIN-challenged mice with SM (LPS/D-GaIN+, Post-SM+), LPS/D-GaIN-challenged mice with dLGG (LPS/D-GaIN+, Post-dLGG+). Data are mean±S.E.M. of results of 6 mice per treatment group. Different letters indicate the significant difference within the tested groups (P<0.05).
Figure 5C:
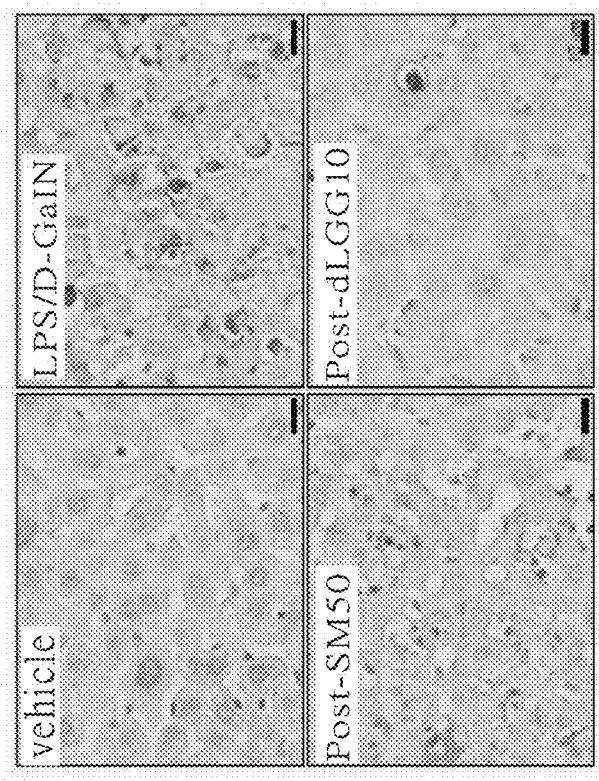
FIG. 5C shows the result of TUNEL assay of liver tissues. Representative image of each treatment group is shown. Brownish cells are TUNEL-positive apoptotic cells.
Figure 5B:
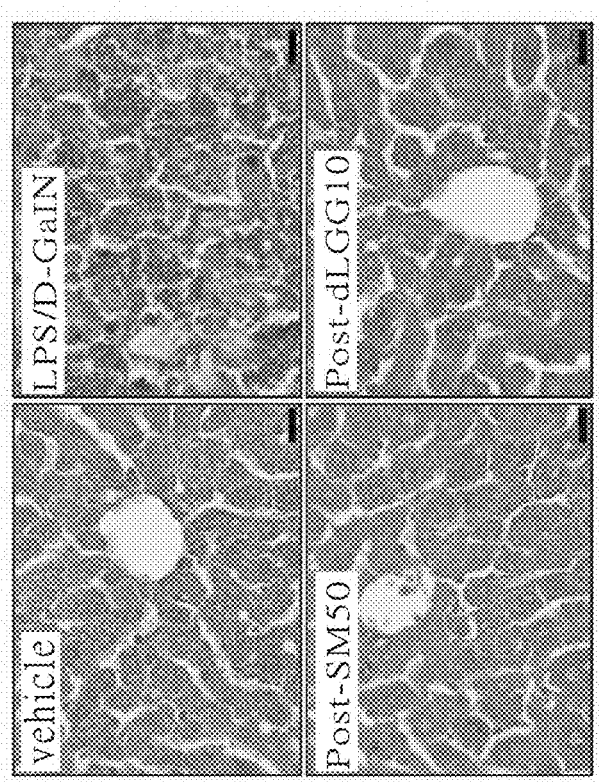
FIG. 5B shows the H&E staining and histology of liver sections from treated mice. Representative image of each treatment group is shown.
Figure 6A:
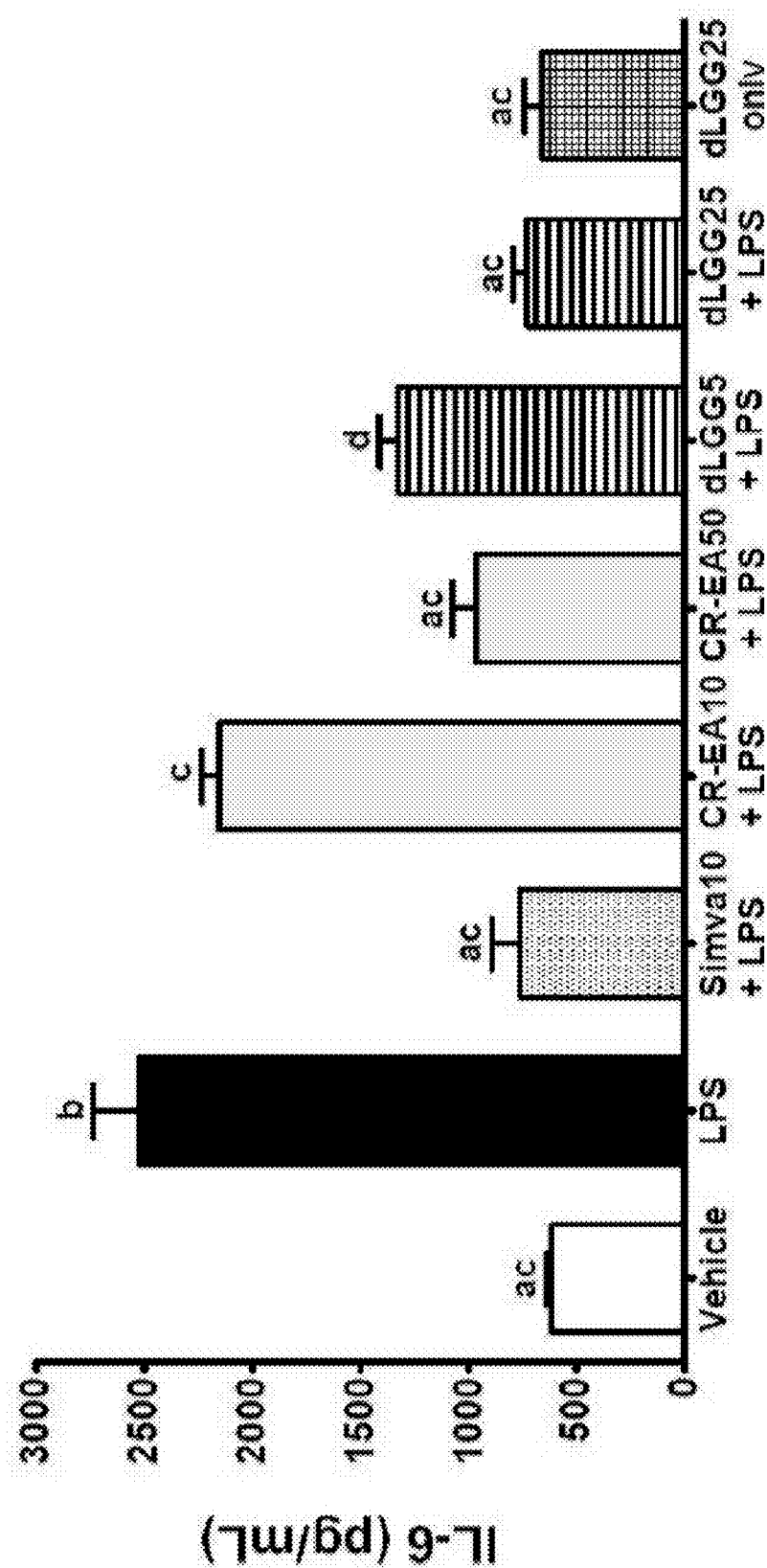
FIG. 6A shows the serum levels of IL-6 in the different treatment groups. Data are mean±SEM (n=4). Different letters indicate the significant difference within the tested groups (P<0.05, ANOVA).
Figure 6B:
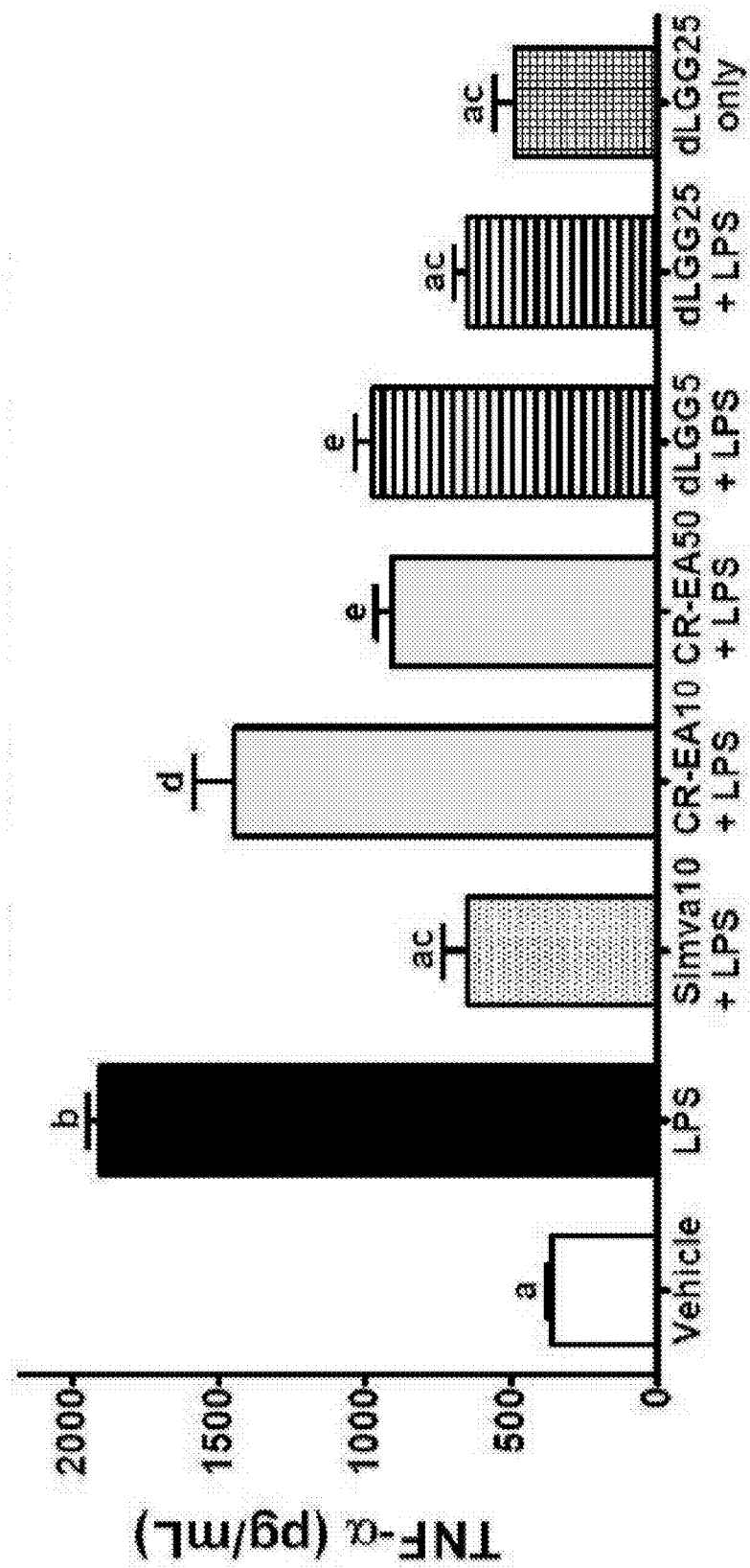
FIG. 6B shows the serum levels of TNF-α in the different treatment groups. Data are mean±SEM (n=4). Different letters indicate the significant difference within the tested groups (P<0.05, ANOVA).
Figure 6C:
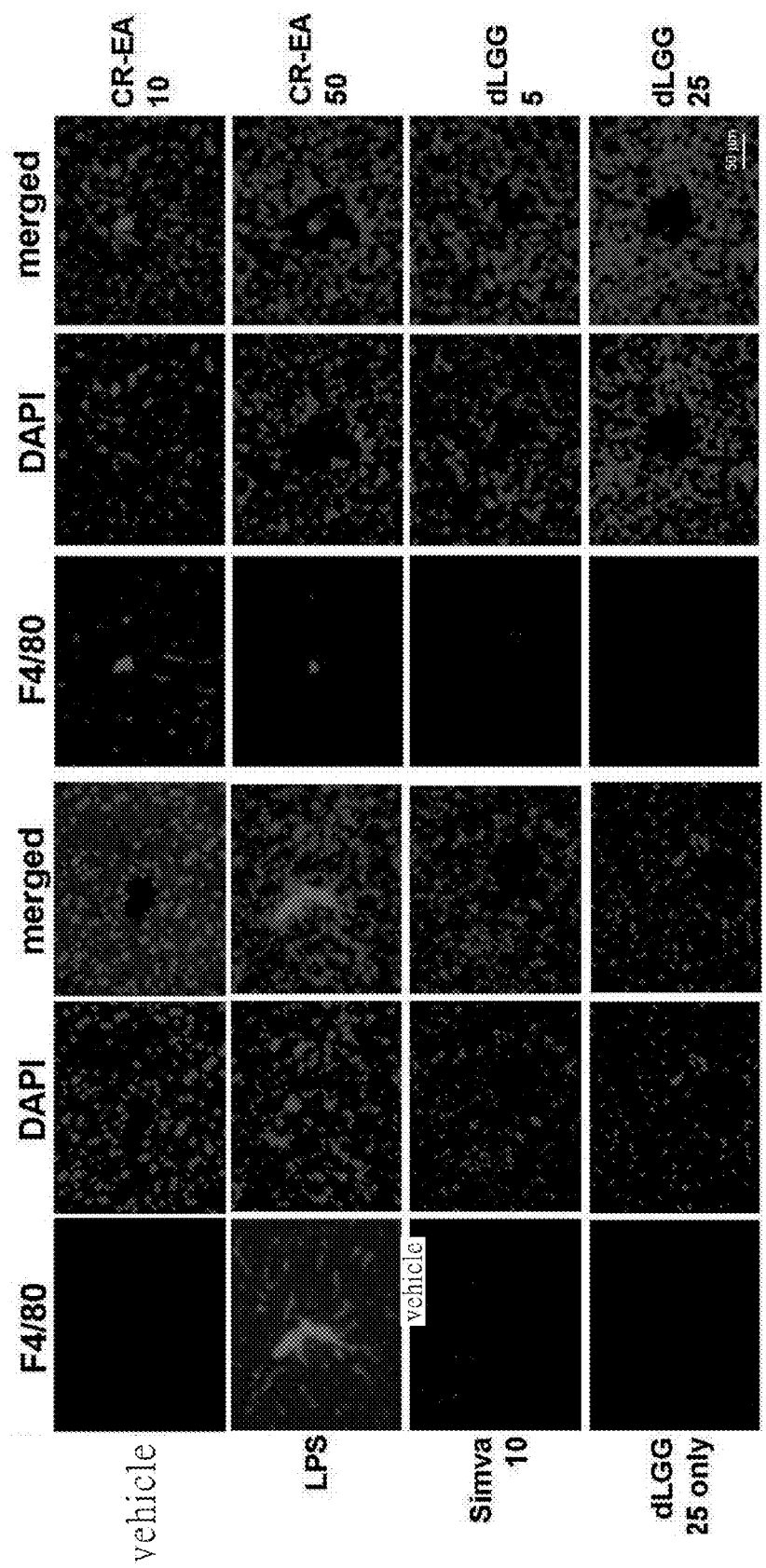
FIG. 6C shows F4/80 immunohistochemistry staining liver sections for illustrating infiltration of macrophage cells. Representative images are shown.
Figure 6D:
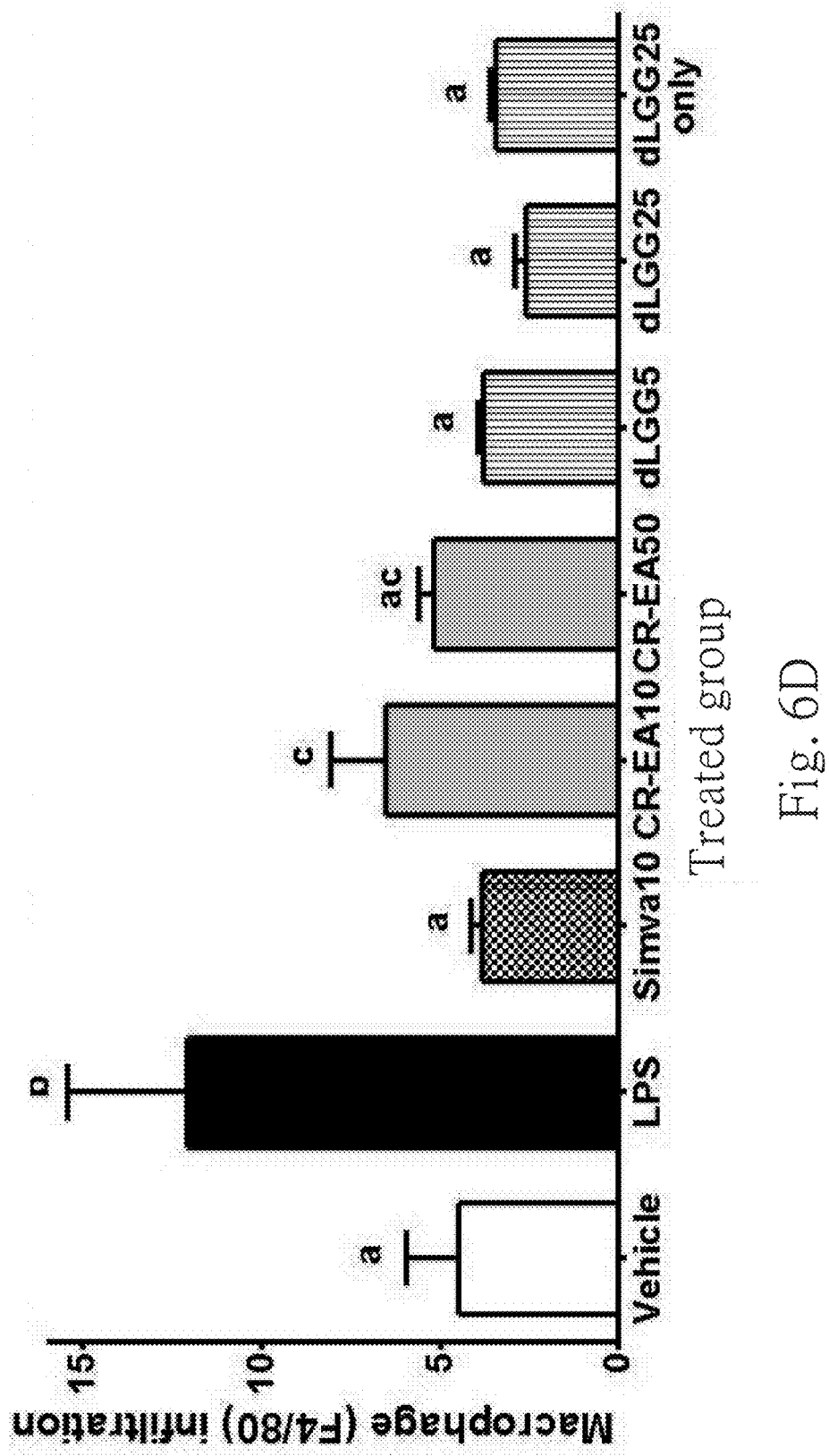
FIG. 6D shows a quantitative comparison among treatment groups determined by mean intensities of F4/80 positive cells.

FIG. 4 and FIG. 5 show the activity assessment result of galactolipids-enriched fraction from GDE and MBE, and pure compound of dLGG. According to FIG. 4A, it shows that GDE, MBE and the hepatoprotective drug SM can effectively reduce the two-fold increase of serum ALT levels in LPS/D-GaIN-challenged mouse compared to the control group. In other words, It proved that the dLGG-enriched galactolipid fractions extracted from MB (MBE) and GD (GDE) are effective to reduce the hepatic injury and acute fulminant hepatitis in LPS/D-GaIN-induced mice.

As shown in FIG. 4B, histopathology examination by H&E staining showed that the observed infiltration of inflammatory cells into liver lobules, tissue destruction and erythrocyte influx of liver tissue etc. in LPD/D-GaIN challenged mice were significantly decreased in the treated groups.

As shown in FIG. 5, it shows that treatment with dLGG after induction of fulminant hepatitis can significantly inhibit the increased levels of serum AST and ALT induced by LPS/D-GaIN in mice, as did by SM. Furthermore, FIG. 5 shows that LPS/D-GaIN-challenged mice liver exhibited infiltration of inflammatory cells into liver lobules, tissue destruction and erythrocyte influx as compared to the vehicle control, and which was attenuated by both dLGG and SM treatment Moreover, dLGG treatment also significantly decreased the numbers of apoptosis cells, TUNEL positive-stained cells in, in liver tissue of mice. Therefore, dLGG is as a therapeutic agent for treating acute fulminant hepatitis of LPS/D-GaIN-challenged mice.

Besides, dLGG still have significant protection effect in mice pre-treated with dLGG (1 or 10 mg/kg) 1 hour before LPS/D-GaIN-challenge (data not shown). These results indicate that dLGG has therapeutic and protective effect against LPS/D-GaIN-induced fulminant hepatic failure. 2.3 Protective and Therapeutic Effect of Galactolipids-Enriched C. rabens Extract and dLGG Against LPS-Induced Inflammation and Sepsis in Mice Acute inflammation will cause serious systemic response including sepsis. Sepsis is a complicate indication that causes rapid organ failure and death. Acute kidney injury (AKI) is a common life-threatening disease that has about 45% mortality in past thirty years, and about half of patients of these severe AKI are triggered by sepsis (Uchino et al., 2005; Yasuda et al., 2006).

Endotoxin is an outer membrane component of Gram-negative bacteria which can induce a serious inflammatory cascade reaction and involve in the pathogenesis of sepsis. Inflammation model constructed by LPS infusion/injection has been widely used to study sepsis (Doi et al., 2009). In the embodiment of this present invention, LPS was used to induce acute inflammation and septic shock to observe and evaluate the protective and therapeutic effect of dLGG (5 and 25 mg/kg weight) and CR-EA (10 and 50 mg/kg weight) by patho-physiological comparison of liver, kidney and lung, by determining the serum levels of inflammatory cytokines, IL-6 and TNF-α, and ALT and AST, indicators of liver damage and hepatotoxicity, and by comparison for the expression levels of hypoxia inducible factor-1α (HIF-1α) and peroxisome-proliferator activating receptor δ (PPAR-δ) involved in the induction of hypoxia and in the production of inflammatory lipid mediators among the treatment groups.

An hour before LPS administration, 0.5% DMSO was treated to control group and 10 mg/kg simvastatin, dLGG and CR-EA were treated to positive control group. Simvastatin, a clinical drug, is a HMG-CoA reductase inhibitor and has clinically beneficial effect on cardiovascular, cerebrovascular and acute and chronic kidney diseases (Epstein et al., 2005; Nissen et al., 2005; Almog, et al., 2004). Statin therapy (statin is a category of HMG-CoA reductase inhibitor drug, wherein simvastatin is one of the category) has effect for preventing sepsis and sepsis-induced acute kidney injury of human and animal (Yasuda et al., 2006). Moreover, one group of mice was treated with dLGG (25 mg/kg) without LPS challenge. All the mice were sacrificed after 24 hours. Mice sera were collected to measure and compare the concentration of IL-6 and TNF-α, and the levels of AST and ALT.

Figure 7A:
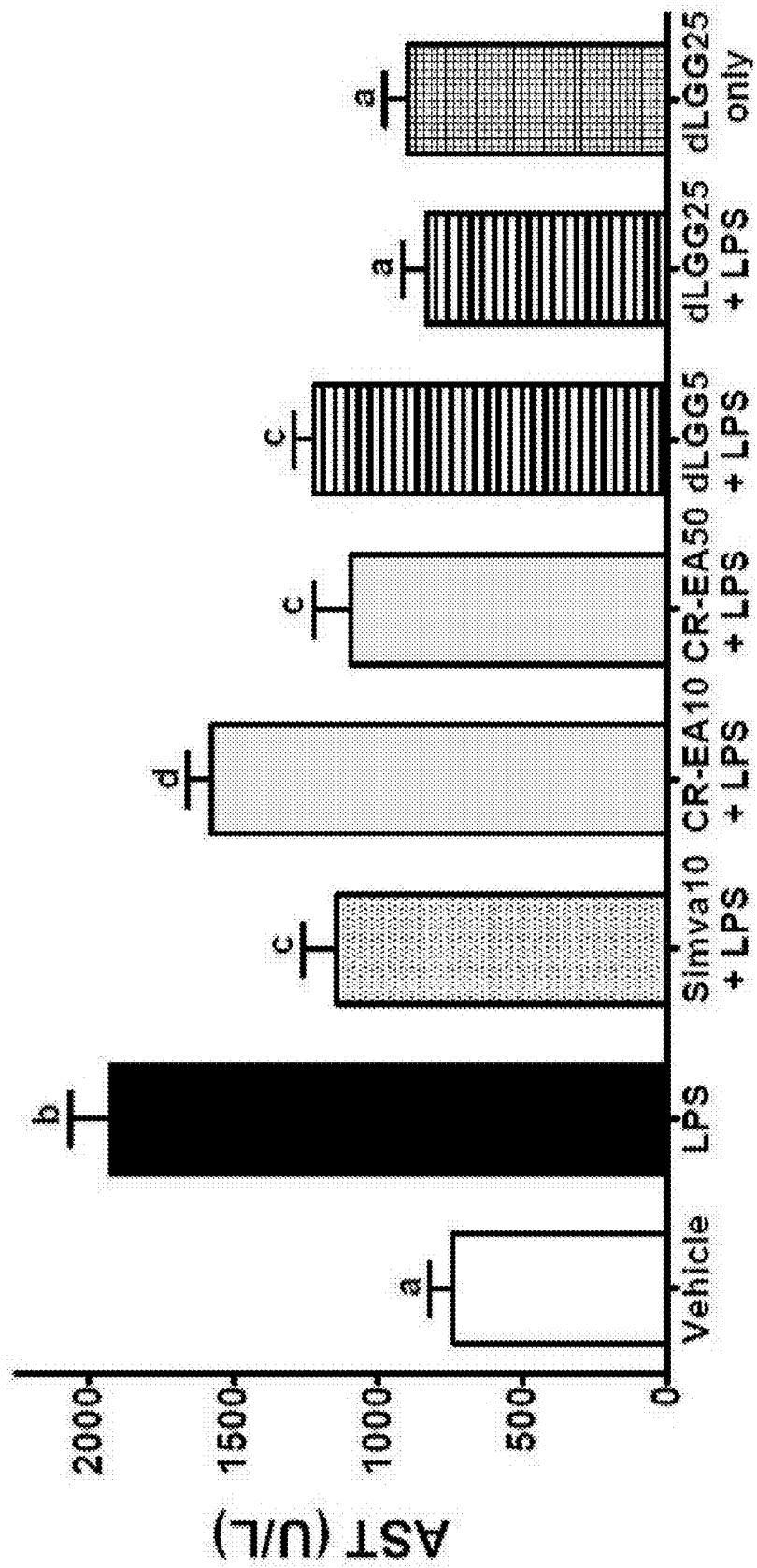
FIG. 7A shows the serum levels of AST in the different treatment groups. Data are mean±SEM (n=4). Different letters indicate the significant difference within the tested groups (P<0.05, ANOVA).
Figure 7B:
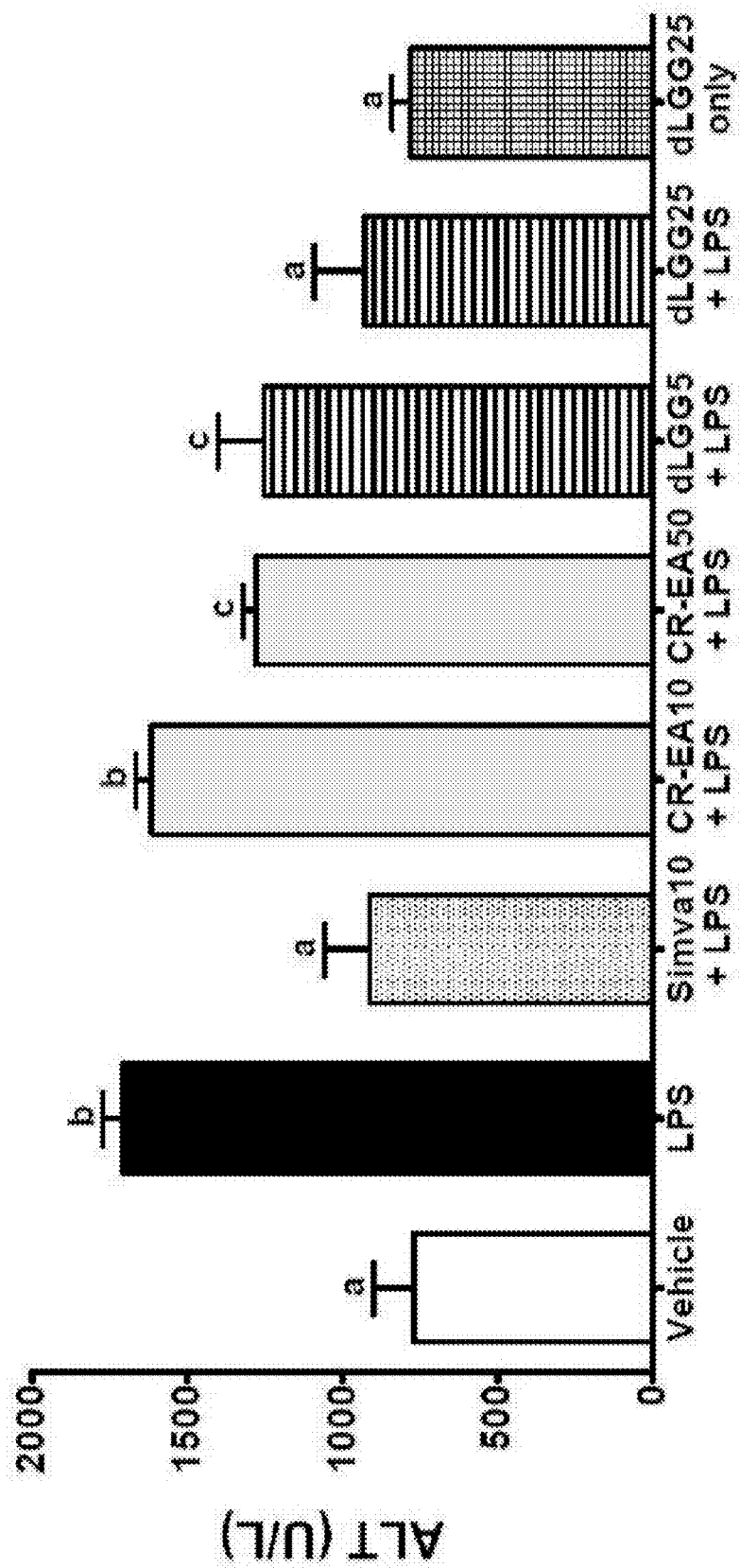
FIG. 7B shows the serum levels of ALT in the different treatment groups. Data are mean±SEM (n=4). Different letters indicate the significant difference within the tested groups (P<0.05, ANOVA).
Figure 7C:
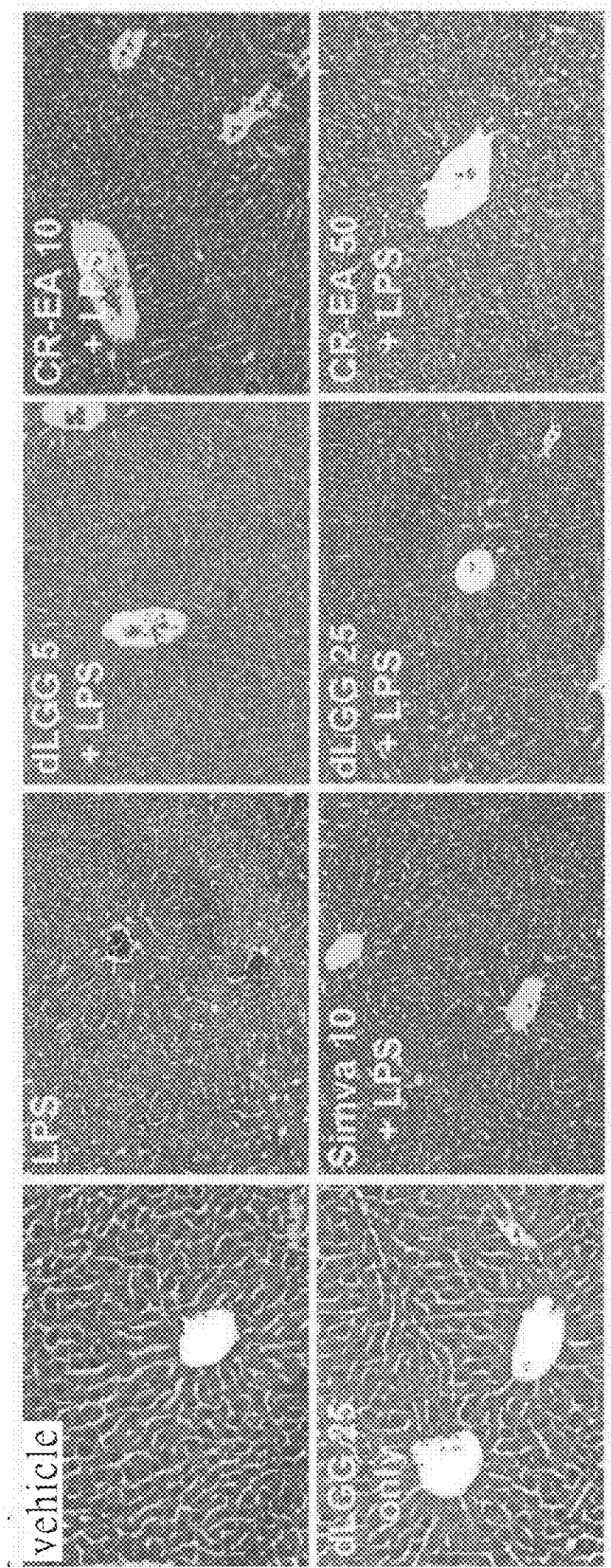
FIG. 7C shows the H&E stained liver sections. It illustrates the results of the liver tissue morphology and red blood cell and inflammatory cell infiltration in different treated groups of LPS-challenged mice. Representative images are shown.

FIG. 6A, FIG. 6B, FIG. 7A and FIG. 7B show that the levels of inflammatory stimulation cytokines in serum significantly decreases in the mice groups treated with CR-EA and dLGG at high dose, respectively, and then by LPS-challenge, wherein after CR-EA and dLGG treated, IL-6 significantly decreases 2.6 and 3.5 times respectively, TNF-α decreases 2.0 and 3.0 times respectively, ALT decreases 1.75 and 2.3 times respectively, and AST decreases 1.3 and 1.8 times respectively. As shown in FIG. 7C, histology comparison of H&E staining between the different treated groups reveals that the inflammatory cells or red blood cell infiltration in liver of mice was induced by LPS-challenge.

Figure 8A:
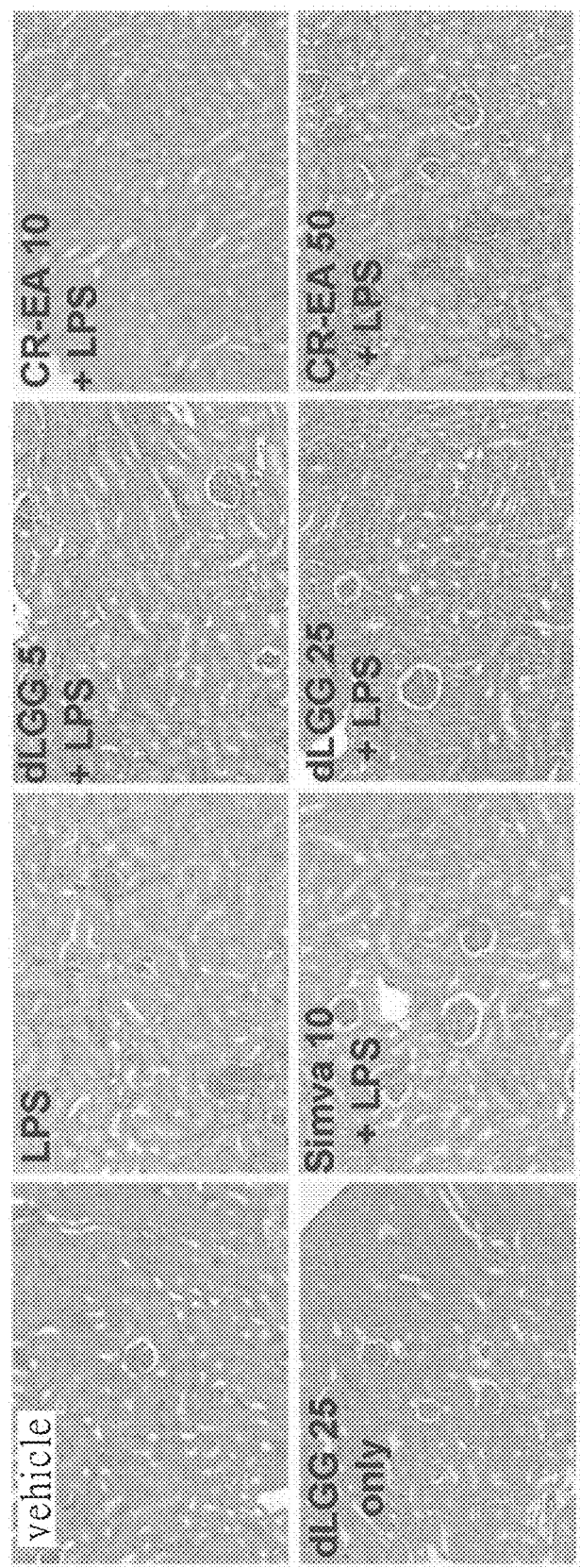
FIG. 8A shows renal histology in the different treatment groups of LPS-challenged mice by H&E-stained kidney sections. Representative images are shown.
Figure 8B:
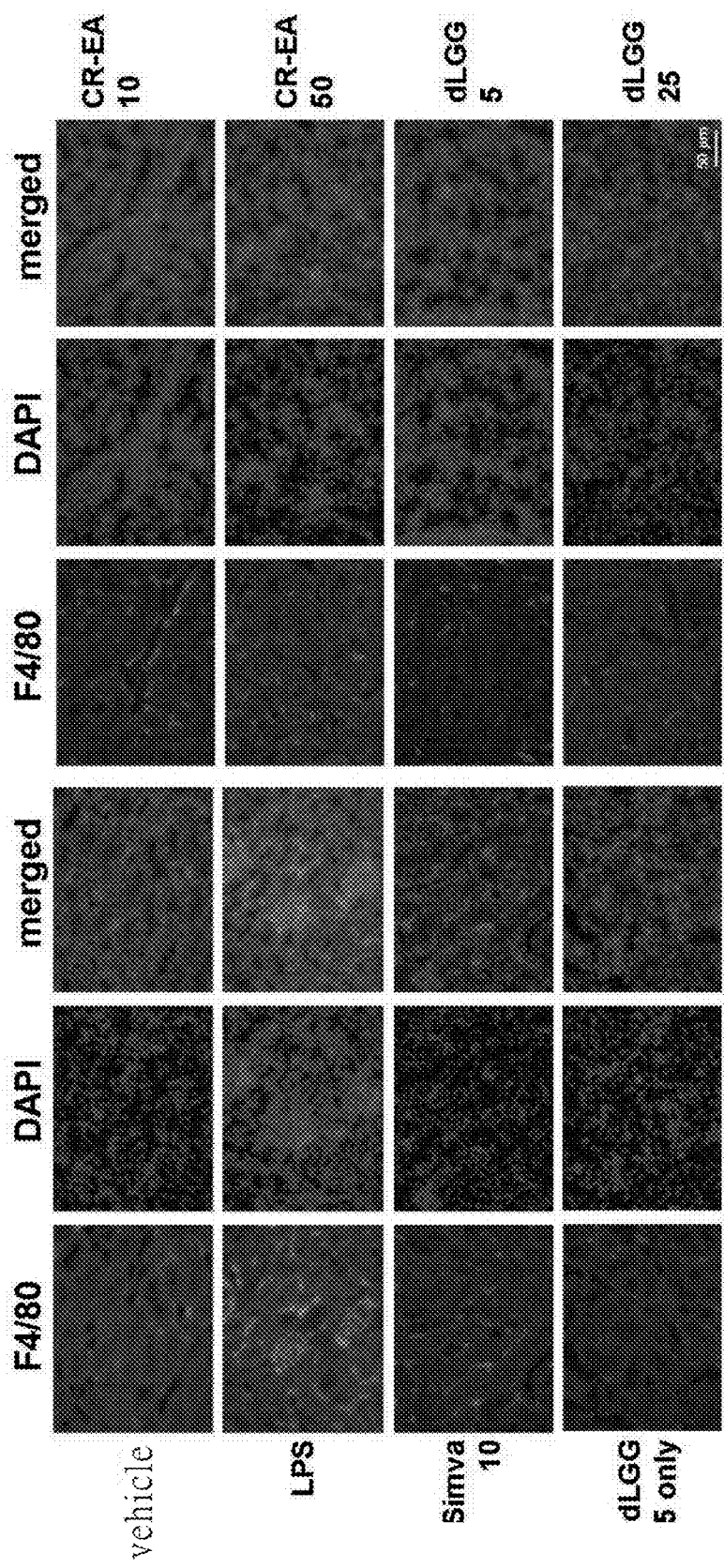
FIG. 8B shows renal infiltration of macrophage cells by F4/80 immunohistochemistry staining of kidney sections. Representative images are shown.
Figure 8C:
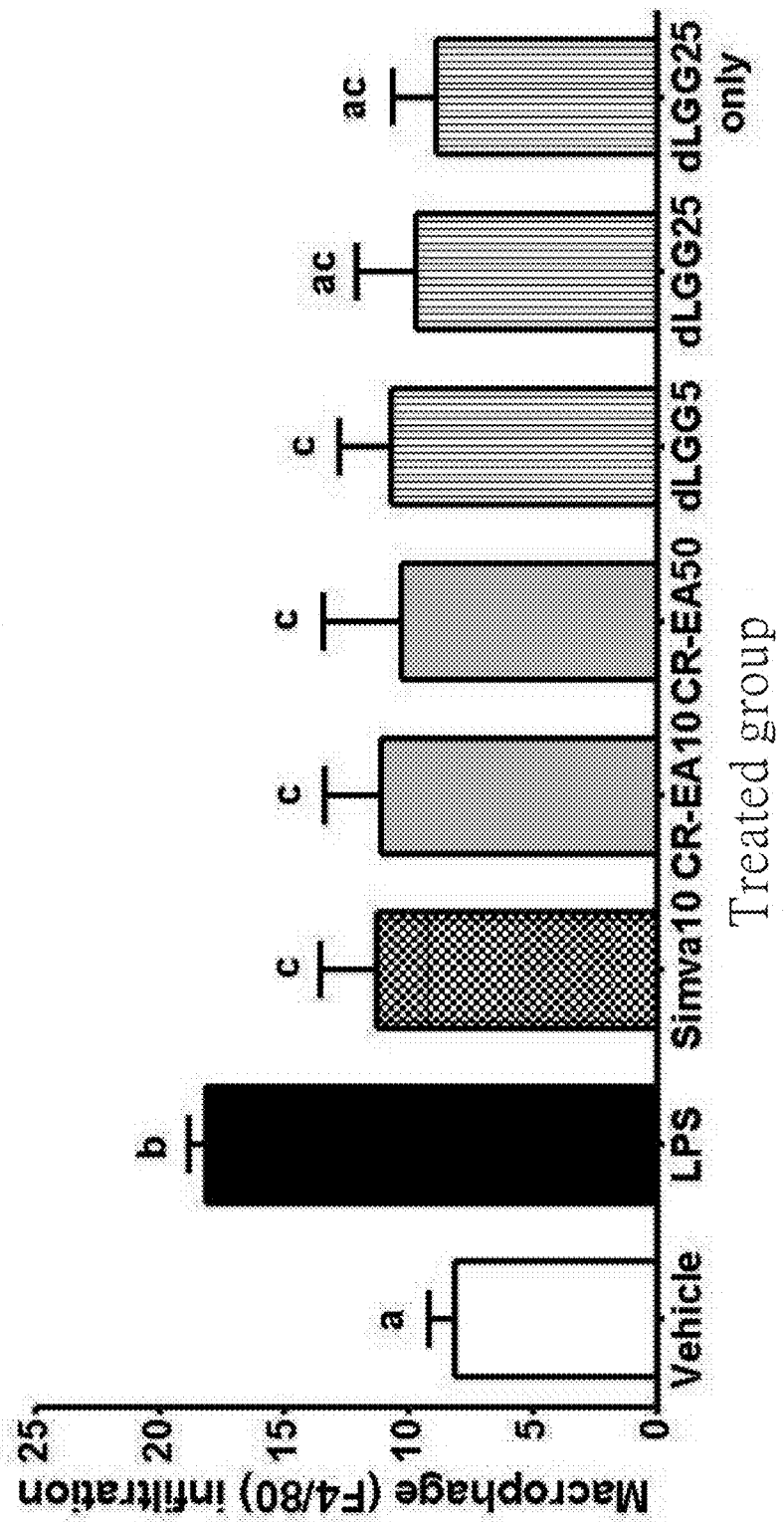
FIG. 8C shows a quantitative comparison among treatment groups determined by mean intensities of F4/80 positive cells.
Figure 9A:
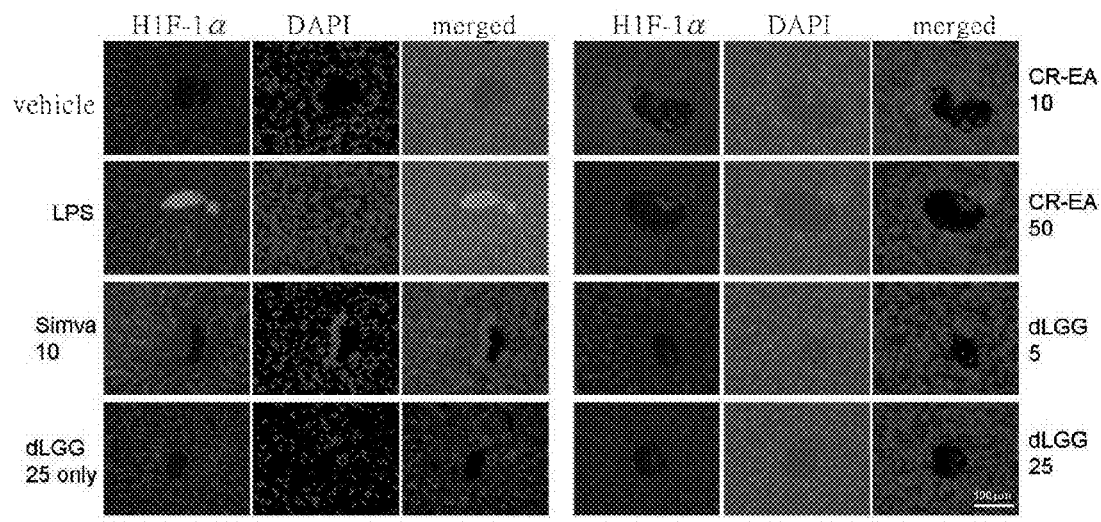
FIG. 9A shows the expression of hypoxia inducible factor-1α (HIF-1α) in different treated groups. Representative images are shown.
Figure 9B:
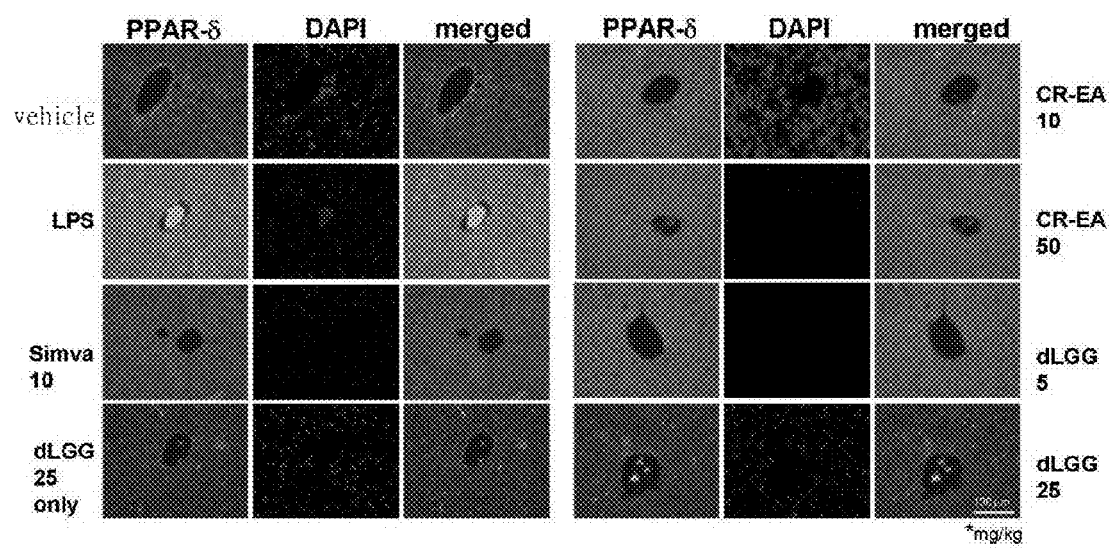
FIG. 9B shows the expression of PPAR-δ in different treated groups. Representative images are shown.
Figure 9C:
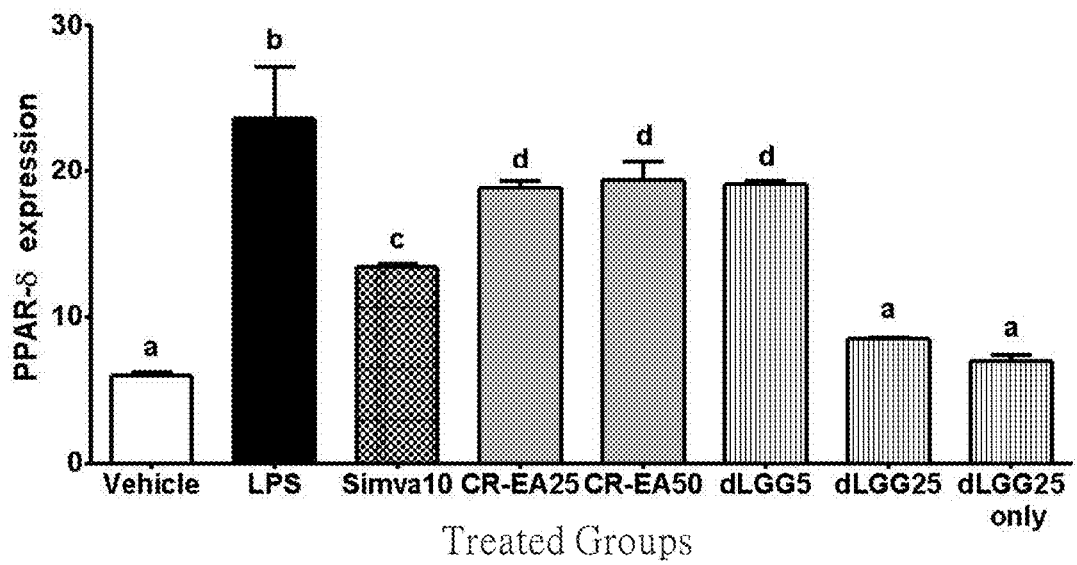
FIG. 9C shows quantitative comparisons among treatment groups determined by mean intensities of HIF-1α expression level.
Figure 9D:
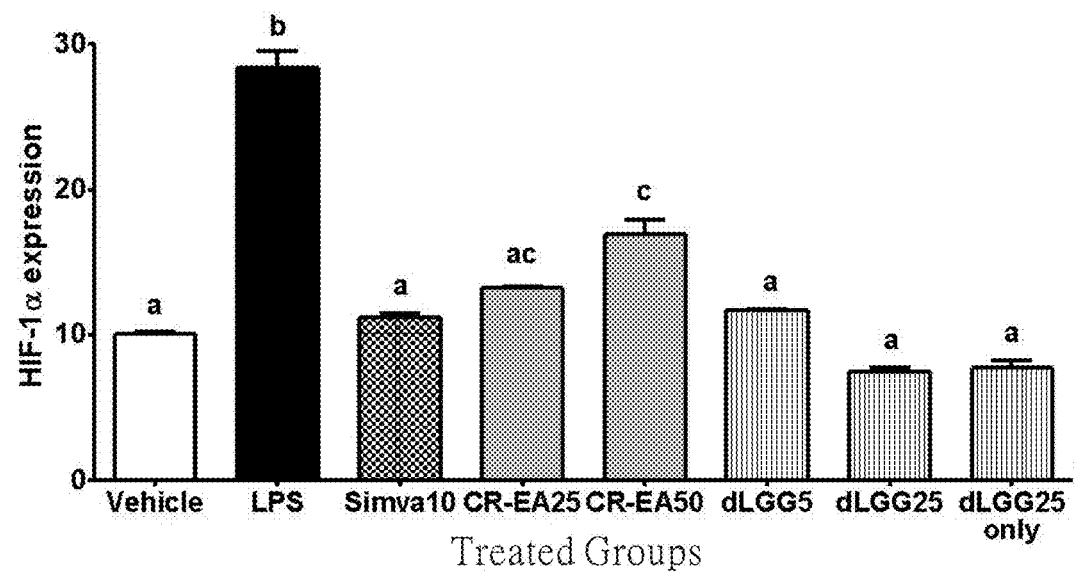
FIG. 9D shows quantitative comparisons among treatment groups determined by mean intensities of PPAR-δ expression level.

FIG. 8A shows the effect of CR-EA and dLGG pre-treated for preventing acute kidney injury. H&E staining result can be observed damage of adrenal cortex, vacuolar degeneration of tubular cells and macrophage infiltration. It has been reported that simvastatin can improve sepsis-induced acute kidney injury and mortality using cecal ligation and puncture operation in mice (Yasuda et al., 2006). The embodiment of this present invention, FIG. 5A can be observed that simvastatin can prevent sepsis-induced acute kidney injury of LPS treated mice, and the same remarkably protective effect can be observed in the CR-EA or dLGG treated group. These effects can be concluded from renal histology of the CR-EA or dLGG-treated group is similar to those of the vehicle control group mice. F4/80 immunohistology staining results show that treatment with CR-EA or dLGG resulted to decreased infiltration and activation of macrophages in liver, as shown in FIG. 8C, in comparison with the vehicle control group. The positive control group (Simva 10) shows similar result in comparison with the CR-EA or dLGG treated group. Furthermore, after LPS-challenge, treatment of dLGG at dose of 25 mg/kg dose can effectively reduce damages in mice liver, lung and kidney caused by LPS (data not shown). According to the above results, it suggests that CR-EA and dLGG have ability to prevent and treat LPS-induced inflammation and sepsis in mice respectively.

FIG. 9A to FIG. 9D further demonstrated that pre-treatment of CR-EA and dLGG will down-regulated the expression of two major proteins, PPAR-δ and HIF-1α, which involve in the formation of inflammatory mediators and induction of hypoxia. These results imply that CR-EA and dLGG treatment can attenuate organ damage caused by oxygen deprivation and hypoxia conditions and may contribute to the regulation of inflammatory lipid mediators in homeostatic levels.

According to FIGS. 6 to 9, it shows that the levels of IL-6, TNF-α, AST and ALT in the sera, pathological evaluations in organ tissues, such as liver and kidney, and expression levels of several protein markers from dLGG treated only mice were similar to those from the vehicle treated mice, as well as lung analysis result (data not shown). These results illustrate that dLGG is harmfulless to mice.

In conclusion, these results show that CR extract and dLGG have potential to be preventive or therapeutic agent against LPS-induced sepsis.

2.4 Depigmentation B16 Cells by dLGG and CR-EA Extract

Skin, being the largest organ of body is always under the influence of internal and external factors. The skin reacts to those stimuli by modifying the constitutive pigmentation pattern. Melanin, a kind of pigment, is responsible for skin color and preventing skin damage or pigmentation induced from environment (ex. UV) or other factors (drugs or chemicals). Melanin is produced through the process of melanogenesis in melanocytes (Costin and Hearing, 2007). The enzyme tyrosinase e is essential in the production of melanin in mammals (Hearing and Tsukamoto, 1991). Microphthalmia-associated transcription factor (MITF) involved in the regulation of melanocyte cell differentiation, pigmentation, proliferation and survival which is also a major transcriptional regulator of genes encoding melanogenic enzymes or proteins, such as tyrosinase, tyrosinase-related protein 1 and protein 2 (Yasumoto et al., 1997; Hasegawa et al., 2010).

A highly pigmented B16 melanoma cell has been used as an experiment model to e study depigmentation effect of compounds from 70's to date (Bang et al., 2013; Wrathall et al., 1973). In the embodiment of this present invention, the EA fractions derived from the total crude water (CR-W-EA) and ethanolic (CR-Et-EA) extracts of *Crassocephalum rabens* were used to examine their ability to depigment B16 cells by direct observation of the cell pellets after treatment. KA and DMSO were used as positive and vehicle control, respectively.

Figure 10A:
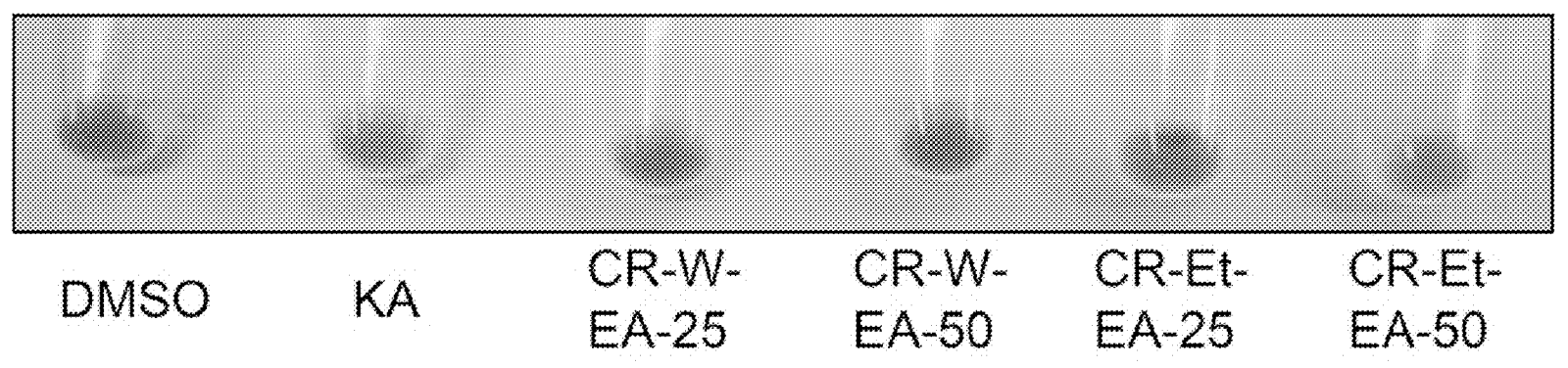
Figures 10B, 10C:
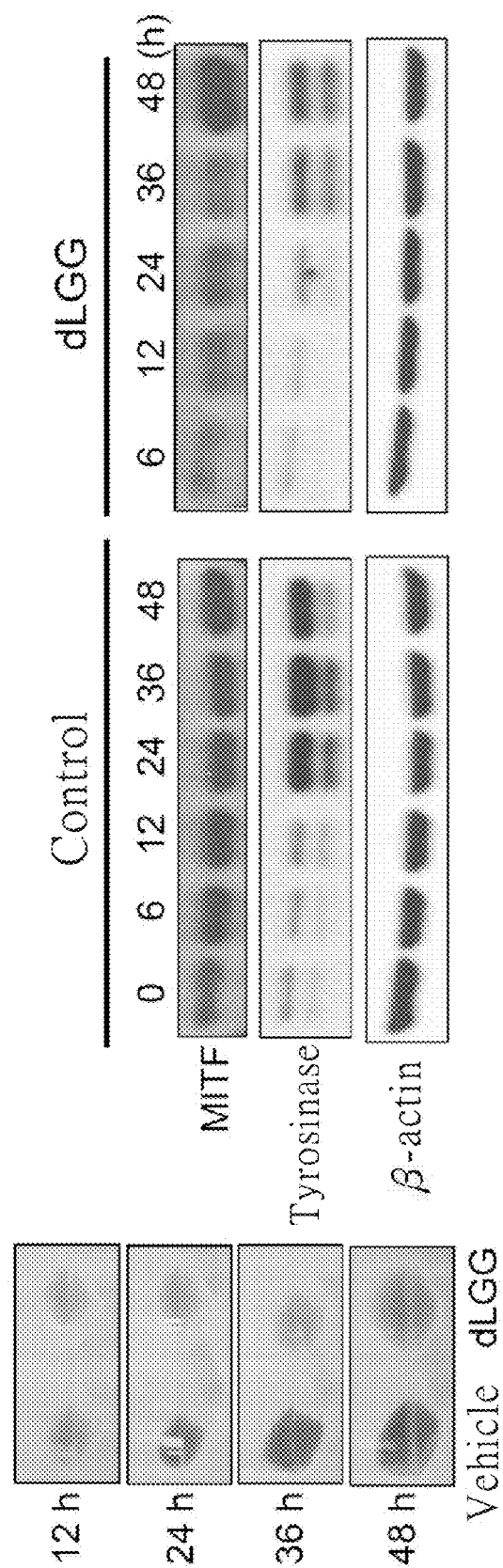
FIG. 10B shows depigmentation in B16 melanoma cells by 45 μM dLGG at different time points.
FIG. 10C shows western blot analysis of the expression of melanogenesis associated protein MITF and tyrosinase with vehicle (control group) or 45 μM dLGG treatment.

FIG. 10(A) shows that CR-Et-EA possesses dose-dependent effect on depigmentation of B16 melanoma cells compare with the vehicle control. The depigmentation effect at different time points of single compound dLGG purified from CR-Et-EA was further assessed. FIG. 10(B) shows that dLGG (45 µM) has significantly depigmentation in a time-dependent manner in B16 melanoma cells compared with the vehicle control group.

Molecular mechanism of dLGG depigmentation effect was further studied. Western blotting assay was preceded for testing the effect of dLGG on tyrosinase and MITF expression. As shown in FIG. 10(C), it shows that dLGG can certainly inhibit the expression of melanogenesis associated protein, MITF and tyrosinase. The data indicate that dLGG inhibit expression of MITF and tyrosinase to suppress melanogenesis that resulted in depigmentation of in B16 melanoma cells, suggesting dLGG can be used as a new skin-whiting agent.

It should be understood that the above-mentioned detailed description and specific examples, while indicating preferred embodiments of the invention, are given by way of illustration only. Various changes and modifications within the spirit and scope of the invention will become apparent to those skilled in the art from this detailed description. All such modifications as would be obvious to one skilled in the art are intended to be included within the scope of the following claims.

What is claimed is:

1. A method of treating a human suffering from acute fulminant hepatitis comprising administering to said human suffering from acute fulminant hepatitis a therapeutically effective amount of a *Crassocephalum rubens* extract, a *murdannia bracteata* extract or a *gynura divaricate* extract which has been extracted with methanol, ethanol or ethyl acetate and which effectively treats the human suffering from acute fulminant hepatitis.

* * * * *